(12) United States Patent
Babcock et al.

(10) Patent No.: US 12,409,253 B2
(45) Date of Patent: *Sep. 9, 2025

(54) LOW PARTICULATE LUBRICIOUS COATING WITH VINYL PYRROLIDONE AND ACIDIC POLYMER-CONTAINING LAYERS

(71) Applicant: Surmodics, Inc., Eden Prairie, MN (US)

(72) Inventors: David E. Babcock, Brooklyn Park, MN (US); Timothy M. Kloke, Victoria, MN (US); Joseph S. McGonigle, Minneapolis, MN (US)

(73) Assignee: Surmodics, Inc., Eden Prairie, MN (US)

(*) Notice: Subject to any disclaimer, the term of this patent is extended or adjusted under 35 U.S.C. 154(b) by 15 days.

This patent is subject to a terminal disclaimer.

(21) Appl. No.: 17/316,244

(22) Filed: May 10, 2021

(65) Prior Publication Data

US 2021/0260255 A1     Aug. 26, 2021

Related U.S. Application Data

(63) Continuation of application No. 14/148,339, filed on Jan. 6, 2014, now Pat. No. 11,000,632.

(60) Provisional application No. 61/783,179, filed on Mar. 14, 2013, provisional application No. 61/748,859, filed on Jan. 4, 2013.

(51) Int. Cl.
| | |
|---|---|
| *A61L 29/14* | (2006.01) |
| *A61L 29/04* | (2006.01) |
| *A61L 29/08* | (2006.01) |
| *B05D 7/00* | (2006.01) |
| *C10M 107/28* | (2006.01) |
| *C10M 107/42* | (2006.01) |
| *C10M 107/46* | (2006.01) |
| *C10M 107/48* | (2006.01) |
| *C10M 107/50* | (2006.01) |
| *C10M 135/36* | (2006.01) |
| *C10M 169/04* | (2006.01) |
| *C10M 177/00* | (2006.01) |
| *C10N 20/00* | (2006.01) |
| *C10N 50/00* | (2006.01) |

(52) U.S. Cl.
CPC ............. *A61L 29/14* (2013.01); *A61L 29/041* (2013.01); *A61L 29/085* (2013.01); *B05D 7/54* (2013.01); *C10M 107/28* (2013.01); *C10M 107/42* (2013.01); *C10M 107/46* (2013.01); *C10M 107/48* (2013.01); *C10M 107/50* (2013.01); *C10M 135/36* (2013.01); *C10M 169/04* (2013.01); *C10M 177/00* (2013.01); *A61L 2400/10* (2013.01); *A61L 2420/02* (2013.01); *A61L 2420/08* (2013.01); *C10M 2209/084* (2013.01); *C10M 2209/0845* (2013.01); *C10M 2217/0245* (2013.01); *C10M 2217/0285* (2013.01); *C10N 2020/01* (2020.05); *C10N 2050/023* (2020.05); *C10N 2050/025* (2020.05); *Y10T 428/31573* (2015.04); *Y10T 428/31699* (2015.04); *Y10T 428/3175* (2015.04); *Y10T 428/31928* (2015.04)

(58) Field of Classification Search
CPC ...... A61L 29/14; A61L 29/041; A61L 29/085; A61L 2400/10; A61L 2420/02; A61L 2420/08; B05D 7/54; C10M 107/28; C10M 107/42; C10M 107/46; C10M 107/48; C10M 107/50; C10M 135/36; C10M 169/04; C10M 177/00; C10M 2209/084; C10M 2209/0845; C10M 2217/0245; C10M 2217/0285; C10N 2020/01; C10N 2050/023; C10N 2050/025; Y10T 428/31573; Y10T 428/31699; Y10T 428/3175; Y10T 428/31928

See application file for complete search history.

(56) References Cited

U.S. PATENT DOCUMENTS

| | | |
|---|---|---|
| 4,979,959 A | 12/1990 | Guire |
| 5,002,582 A | 3/1991 | Guire et al. |
| 5,061,424 A | 10/1991 | Karimi et al. |
| 5,263,992 A | 11/1993 | Guire |
| 5,382,234 A | 1/1995 | Cornelius et al. |
| 5,414,075 A | 5/1995 | Swan et al. |
| 5,512,329 A | 4/1996 | Guire et al. |

(Continued)

FOREIGN PATENT DOCUMENTS

| | | |
|---|---|---|
| JP | 10110134 A | 4/1998 |
| WO | 03/055611 A1 | 10/2003 |

(Continued)

OTHER PUBLICATIONS

Yang, et al. (2007) "The influence of pH on a hydrogen-bonded assembly film", Soft Matter, 3:463-469.

(Continued)

*Primary Examiner* — Sarah Alawadi
*Assistant Examiner* — Thurman Wheeler
(74) *Attorney, Agent, or Firm* — Kagan Binder, PLLC

(57) ABSTRACT

A lubricious coating for a medical device is formed including first and second coated layers. The first coated layer is between the second coated layer and the device surface and includes a vinyl pyrrolidone polymer and a photo reactive group. The second coated layer is in direct contact with the first coated layer and is a top coating that includes an acrylic acid polymer. The second coated layer can optionally include photoreactive groups. The coating was found to have a very low number of particulates (e.g., 10 μm or greater) which is very desirable for in vivo use.

17 Claims, 10 Drawing Sheets

Specification includes a Sequence Listing.

(56) References Cited

U.S. PATENT DOCUMENTS

| | | |
|---|---|---|
| 5,571,089 A | 11/1996 | Crocker |
| 5,637,460 A | 6/1997 | Swan et al. |
| 5,714,360 A | 2/1998 | Swan et al. |
| 5,776,101 A | 7/1998 | Goy |
| 5,807,331 A | 9/1998 | Heijer et al. |
| 5,858,653 A | 1/1999 | Duran et al. |
| 5,882,336 A | 3/1999 | Janacek |
| 6,156,345 A | 12/2000 | Chudzik et al. |
| 6,393,589 B1 | 5/2002 | Smit et al. |
| 6,394,995 B1 | 5/2002 | Solar et al. |
| 6,517,515 B1 | 2/2003 | Eidenschink |
| 6,623,504 B2 | 9/2003 | Vrba et al. |
| 6,818,018 B1 | 11/2004 | Sawhney |
| 7,772,393 B2 | 8/2010 | Guire et al. |
| 8,487,137 B2 | 7/2013 | Guire et al. |
| 8,513,320 B2 | 8/2013 | Rooijmans |
| 8,809,411 B2 | 8/2014 | Rooijmans |
| 8,889,760 B2 | 11/2014 | Kurdyumov et al. |
| 9,173,974 B2 | 11/2015 | Görne et al. |
| 9,321,030 B2 | 4/2016 | Sukhishvili et al. |
| 9,321,872 B2 | 4/2016 | Minagawa |
| 9,550,011 B2 | 1/2017 | Xie |
| 10,780,199 B2 | 9/2020 | Gilman |
| 11,000,632 B2 | 5/2021 | Babcock et al. |
| 2001/0011165 A1 | 8/2001 | Engelson et al. |
| 2008/0213334 A1 | 9/2008 | Lockwood et al. |
| 2009/0123519 A1 | 5/2009 | Rolfes et al. |
| 2010/0198168 A1 | 8/2010 | Rooijmans |
| 2011/0059874 A1 | 3/2011 | Rooijmans et al. |
| 2011/0144373 A1 | 6/2011 | Swan et al. |
| 2011/0245367 A1 | 10/2011 | Kurdyumov et al. |
| 2012/0077049 A1 | 3/2012 | Lin |
| 2012/0114589 A1 | 5/2012 | Rolfes-Meyering et al. |
| 2012/0149934 A1 | 6/2012 | Kurdyumov |
| 2013/0143056 A1 | 6/2013 | Swan et al. |
| 2013/0197433 A1 | 8/2013 | Babcock |
| 2013/0202833 A1 | 8/2013 | Belt et al. |
| 2013/0261566 A1 | 10/2013 | Lockwood et al. |
| 2013/0337147 A1 | 12/2013 | Chappa et al. |
| 2014/0162083 A1 | 6/2014 | Kurdyumov et al. |
| 2014/0193474 A1 | 7/2014 | Babcock et al. |
| 2015/0352259 A1 | 12/2015 | Rooijmans et al. |
| 2016/0053063 A1 | 2/2016 | Schroter et al. |
| 2016/0310643 A1 | 10/2016 | Dias et al. |
| 2022/0211917 A1 | 7/2022 | Militello |

FOREIGN PATENT DOCUMENTS

| | | |
|---|---|---|
| WO | 2008/104573 A2 | 4/2008 |
| WO | 2011/123441 A1 | 6/2011 |
| WO | 2015029625 A1 | 3/2015 |

OTHER PUBLICATIONS

Barnwell, et al. (1997) "Foreign bodies in small arteries after use of an infusion microcatheter", American Journal of Neuroradiology, 18:1886-1889.

Bimendina, et al. (1976) "Poly(acrylic acid)—poly(vinyl pyrrolidone) complexes in solutions", Chemical Zvesti, 30(3):301-305.

Chun, et al. (2004) "Characteristics of poly(vinyl pyrrolidone)/poly(acrylic acid) interpolymer complex prepared by template polymerization of acrylic acid: Effect of reaction solvent and molecular weight of template", Journal of Applied Polymer Science, 94(6):2390-2394.

Fealey et al. (2008) "Complications of endovascular polymers associated with vascular introducer sheaths and metallic coils in 3 patients, with literature review" The American Journal of Surgical Pathology, 32:1310-1316.

Gina-Gubriela Bumbu et al. (2009) "Interpolymer Complexes Containing Copolymers", Hydrogen-Bonded Interpolymer Complexes, Chapter 7, 173-200.

Iliopoulos (1988), Journal of Polymer Science Part A Polymer Chemistry, p. 463.

Khutoryanski, et al. (2009) "pH and Ionic Strength Effects on Interpolymer Complexation Via Hydrogen-Bonding", Hydrogen-Bonded Interpolymer Complexes Chapter 1, 1-5.

Mehta, et al. (2010) "Hydrophilic polymer emboli: an under-recognized iatrogenic cause of ischemia and infarct", Modern Pathology, 23:921-930.

```
                        SEQUENCE LISTING

<160> NUMBER OF SEQ ID NOS: 46

<210> SEQ ID NO 1
    <211> LENGTH: 5
    <212> TYPE: PRT
    <213> ORGANISM: Artificial Sequence
    <220> FEATURE:
    <223> OTHER INFORMATION: chemically synthesized peptide

<400> SEQUENCE: 1

Tyr Ile Gly Ser Arg
    1               5

<210> SEQ ID NO 2
    <211> LENGTH: 4
    <212> TYPE: PRT
    <213> ORGANISM: Artificial Sequence
    <220> FEATURE:
    <223> OTHER INFORMATION: chemically synthesized peptide

<400> SEQUENCE: 2

Asp Gly Glu Ala
    1

<210> SEQ ID NO 3
    <211> LENGTH: 5
    <212> TYPE: PRT
    <213> ORGANISM: Artificial Sequence
    <220> FEATURE:
    <223> OTHER INFORMATION: chemically synthesized peptide

<400> SEQUENCE: 3

Lys Asp Gly Glu Ala
    1               5

<210> SEQ ID NO 4
    <211> LENGTH: 6
    <212> TYPE: PRT
    <213> ORGANISM: Artificial Sequence
    <220> FEATURE:
    <223> OTHER INFORMATION: chemically synthesized peptide
    <220> FEATURE:
    <221> NAME/KEY: misc_feature
    <222> LOCATION: (3)..(3)
    <223> OTHER INFORMATION: Xaa = hydroxyproline

<400> SEQUENCE: 4

Gly Phe Xaa Gly Glu Arg
    1               5

<210> SEQ ID NO 5
    <211> LENGTH: 5
    <212> TYPE: PRT
    <213> ORGANISM: Artificial Sequence
    <220> FEATURE:
    <223> OTHER INFORMATION: chemically synthesized peptide

<400> SEQUENCE: 5
```

```
Leu Arg Gly Asp Asn
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 6

Ile Lys Val Ala Val
1               5

<210> SEQ ID NO 7
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 7

Tyr Phe Gln Arg Tyr Leu Ile
1               5

<210> SEQ ID NO 8
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 8

Cys Asp Pro Gly Tyr Ile Gly Ser Arg
1               5

<210> SEQ ID NO 9
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 9

Pro Asp Ser Gly Arg
1               5

<210> SEQ ID NO 10
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 10

Arg Asn Ile Ala Glu Ile Ile Lys Asp Ala
1               5                   10

<210> SEQ ID NO 11
<211> LENGTH: 13
<212> TYPE: PRT
<213> ORGANISM: Artificial Sequence
<220> FEATURE:
<223> OTHER INFORMATION: chemically synthesized peptide

<400> SEQUENCE: 11
```

Arg Gln Val Phe Gln Val Ala Tyr Ile Ile Ile Lys Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 12

Arg Lys Arg Leu Gln Val Gln Leu Ser Ile Arg Thr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 13

Gly Arg Gly Asp Ser Pro
1               5

<210> SEQ ID NO 14
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 14

Arg Gly Asp Ser
1

<210> SEQ ID NO 15
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 15

Arg Gly Asp Thr
1

<210> SEQ ID NO 16
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 16

Gly Arg Gly Asp
1

<210> SEQ ID NO 17
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 17

Gly Arg Gly Asp Ser 1               5

<210> SEQ ID NO 18
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 18

Gly Arg Gly Asp Gly
1               5

<210> SEQ ID NO 19
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 19

Gly Arg Gly Asp Ser Gly
1               5

<210> SEQ ID NO 20
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 20

Gly Arg Gly Asp Asn Pro
1               5

<210> SEQ ID NO 21
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 21

Gly Arg Gly Asp Ser Pro Lys
1               5

<210> SEQ ID NO 22
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 22

Gly Arg Gly Asp Ser Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 23

Tyr Arg Gly Asp Ser
1               5

```
<210> SEQ ID NO 24
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 24

Tyr Arg Gly Asp Gly
1               5

<210> SEQ ID NO 25
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 25

Tyr Gly Arg Gly Asp
1               5

<210> SEQ ID NO 26
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 26

Cys Gly Arg Gly Asp Ser Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: chemically synthesized peptide

<400> SEQUENCE: 27

Cys Gly Arg Gly Asp Ser Pro Lys
1               5

<210> SEQ ID NO 28
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 28

Tyr Ala Val Thr Gly Arg Gly Asp Ser
1               5

<210> SEQ ID NO 29
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 29

Arg Gly Asp Ser Pro Ala Ser Ser Lys Pro
1               5                   10
```

```
<210> SEQ ID NO 30
<211> LENGTH: 11
<212> TYPE: PRT
<213> ORGANISM: Artificial Sequence
<220> FEATURE:
<223> OTHER INFORMATION: chemically synthesized peptide

<400> SEQUENCE: 30

Gly Arg Gly Asp Ser Pro Ala Ser Ser Lys Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: chemically synthesized peptide

<400> SEQUENCE: 31

Gly Cys Gly Tyr Gly Arg Gly Asp Ser Pro Gly
1               5                   10

<210> SEQ ID NO 32
<211> LENGTH: 18
<212> TYPE: PRT
<213> ORGANISM: Artificial Sequence
<220> FEATURE:
<223> OTHER INFORMATION: chemically synthesized peptide

<400> SEQUENCE: 32

Gly Gly Gly Pro His Ser Arg Asn Gly Gly Gly Gly Gly Gly Arg Gly
1               5                   10                  15

Asp Gly

<210> SEQ ID NO 33
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 33

Arg Gly Asp Val
1

<210> SEQ ID NO 34
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 34

Arg Gly Asp Phe
1

<210> SEQ ID NO 35
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 35

Gly Arg Gly Asp Phe
1               5
```

```
<210> SEQ ID NO 36
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 36

Gly Arg Gly Asp Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 37

Gly Arg Gly Asp Val Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 38

Gly Arg Gly Asp Tyr Pro Cys
1               5

<210> SEQ ID NO 39
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 39

Arg Glu Asp Val
1

<210> SEQ ID NO 40
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 40

Glu Ile Leu Asp Val
1               5

<210> SEQ ID NO 41
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 41

Lys Gln Ala Gly Asp Val
1               5
```

-continued

```
<210> SEQ ID NO 42
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 42

Val Ala Pro Gly
1

<210> SEQ ID NO 43
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 43

Val Gly Val Ala Pro Gly
1               5

<210> SEQ ID NO 44
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 44

Val Ala Val Ala Pro Gly
1               5

<210> SEQ ID NO 45
<211> LENGTH: 8
<212> TYPE: PRT
<213> ORGANISM: Artificial Sequence
<220> FEATURE:
<223> OTHER INFORMATION: chemically synthesized peptide

<400> SEQUENCE: 45

Trp Gln Pro Pro Arg Ala Arg Ile
1               5

<210> SEQ ID NO 46
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 46

Ser Val Val Tyr Gly Leu Arg
1               5
```

LOW PARTICULATE LUBRICIOUS COATING WITH VINYL PYRROLIDONE AND ACIDIC POLYMER-CONTAINING LAYERS

CROSS-REFERENCE TO RELATED APPLICATIONS

The present non-provisional Applications is a continuation of application Ser. No. 14/148,339, filed Jan. 6, 2014, which claims the benefit of commonly owned provisional applications having Ser. No. 61/748,859, filed on Jan. 4, 2013, entitled LUBRICIOUS COATINGS WITH LOW PARTICULATES, and Ser. No. 61/783,179, fled on Mar. 14, 2013, entitled LUBRICIOUS COATING WITH LOW PARTICULATES, which applications are incorporated herein by reference in their entirety. Also, the entire contents of the ASCII text file entitled "SRM0161US3_Sequence_Listing_ST25txt" created on Jan. 6, 2014, having a size of 9 kilobytes is incorporated herein by reference.

FIELD

The present disclosure relates to lubricious coatings. More specifically, the present disclosure relates to lubricious medical device coatings with low particulate generation and medical devices and methods relating to the same.

BACKGROUND

Medical devices include, amongst others, those that are chronically implanted, devices that are transitorily implanted, and those that not implanted at all. Many types of medical devices are enhanced by reducing the friction between the device and the environment that surrounds the medical device, particularly during insertion of a device. One example is catheters that are inserted, at least transitorily, into the body of a subject. Reduction of friction can lead to enhanced patient comfort, procedural ease for the care provider, reduced chances for infection, as well as reduced tissue disruption, amongst other benefits. One approach to reducing the friction between a medical device and the environment surrounding the medical device is to apply a lubricious coating onto the medical device.

SUMMARY OF THE INVENTION

Embodiments of the disclosure include lubricious coatings. Generally, the coatings include a first coated layer including a vinyl pyrrolidone polymer and a photoreactive group, and a second coated layer that is a top coat that includes an acid group-containing polymer, with the first coated layer being between the second coated layer and a substrate surface. In one embodiment the lubricious coating comprises a first coated layer comprising a vinyl pyrrolidone polymer and photoreactive groups. In the first coated layer, the photoreactive groups can be pendent from the vinyl pyrrolidone polymer, pendent on a first cross-linking agent, or both. The coating also comprises a second coated layer that is a top coating comprising an acrylic acid polymer. The second coated layer can optionally comprise photoreactive groups, such as photoreactive groups present on a second cross-linking agent. In the coating the second coated layer is in direct contact with the first coated layer and the first coated layer is between the second coated layer and a substrate surface. In some embodiments the first coated layer is a base coat on a substrate surface.

The coating can include hydrogen bonding between the vinyl pyrrolidone polymer of the first coated layer and the acid group-containing polymer (e.g., acrylic acid polymer) of the second coated layer. By including hydrogen bonding between materials of the first and second layer distinct coating advantages such as greater mechanical strength, reflected by sustained higher compression forces without fragmentation (release of particulates), and also increased lubricity.

Advantageously, the coating including first and second coated layers with the vinyl pyrrolidone polymer and acid group-containing polymer (e.g., acrylic acid polymer) acrylic acid polymer can have a very low number of particulates (e.g., 10 µm or greater). A medical device having a hydrophilic coating with low particulate levels is very desirable for in vivo use. In some embodiments, the coating has a particle count of 20,000 or less, 10,000 or less, or 5,000 or less per 600 mm$^2$ of coated surface, with the coating having a thickness in the range of 100 nm to 10 µm, the particle count based on particles having a size of 10 µm or greater.

In another embodiment, the disclosure provides an implantable or insertable medical device having a coating comprising a coated layer in contact with device material, the device material formed of a melt-extruded composition comprising a vinyl pyrrolidone polymer and a thermoplastic elastomer, wherein the coated layer comprises an acid group-containing polymer, such as an acrylic acid polymer. The acid group-containing polymer in the coated layer is able to undergo hydrogen bonding with the vinyl pyrrolidone polymer in the extruded device material. Optionally, the extruded, coated device can include one or more of the following materials: a vinyl pyrrolidone polymer comprising a photo reactive group, a first cross-linking agent comprising at least two photoreactive groups, and/or a second cross-linking agent comprising at least two photoreactive groups.

In another embodiment, the disclosure provides a method for coating a medical device, comprising a step of melt extruding a composition comprising a vinyl pyrrolidone polymer and a thermoplastic elastomer to form a portion of, or all of, an implantable or insertable medical device having a surface. Next, a step of applying a coating composition comprising an acid group-containing polymer, such as an acrylic acid polymer, to the surface of the device is performed. Application of the coating is performed by moving the extruded device through an acid group-containing polymer-containing coating bath, or applying an acid group-containing polymer to the device surface after moving the extruded device though an aqueous cooling bath. An optional step of treating the coating device with UV irradiation can be performed if the extruded material and/or coating includes a UV activatable photogroup, such as in the form of first and/or second UV activated crosslinking agents.

In some embodiments, the photoreactive groups can be present on first, second, or both first and second crosslinking agents. The first and second cross-linking agents may comprise sodium bis[(4-benzoylphenyl) phosphate. In other embodiments, the first and second cross-linking agents may comprise a linking agent having formula Photo$^1$LG-Photo$^2$, wherein Photo$^1$ and Photo$^2$ independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

The first and second cross-linking agents may comprise a linking agent having a formula selected from (a):

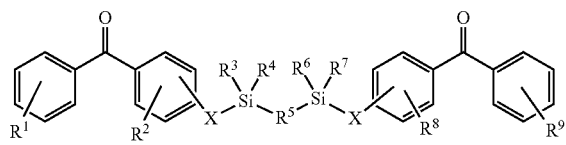

wherein $R^1$, $R^2$, $R^8$ and $R^9$ are any substitution; $R^3$, $R^4$, $R^6$ and $R^7$ are alkyl, aryl, or a combination thereof, $R^5$ is any substitution; and each X, independently, is O, N, Se, S, or alkyl, or a combination thereof, (b):

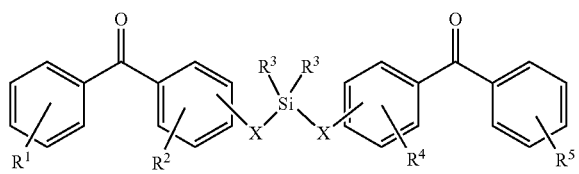

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl, or a combination thereof; (c):

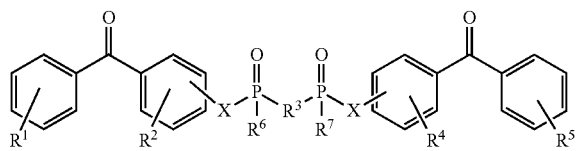

wherein $R^1$, $R^2$, $R^4$ and $R^5$ are any substitution; $R^3$ is any substitution; $R^6$ and $R^7$ are alkyl, aryl, or a combination thereof; and each X, independently, is O, N, Se, S, alkyl, or a combination thereof; and (d):

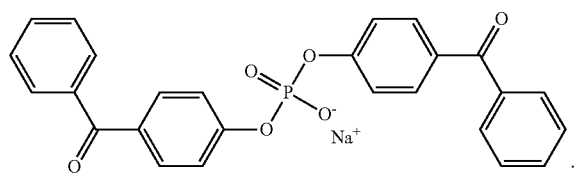 [SMILES: O=C(c1ccccc1)c1ccc(OP(=O)([O-])Oc2ccc(C(=O)c3ccccc3)cc2)cc1 ; [Na+]]

In other embodiments, the first and/or second cross-linking agent(s) can be ionic photoactivatable cross-linking agents of formula I: $X^1$—Y—$X^2$ where Y is a radical containing at least one acidic group, basic group, or a salt of an acidic group or basic group, with $X^1$ and $X^2$ are each independently a radical containing a latent photoreactive group. Acidic groups include sulfonic acids, carboxylic acids, phosphonic acids, and the like, and salts of such groups include, for example, sulfinate, carboxylate, and phosphate salts. Basic groups include, for example, ammonium, phosphonium, and sulfonium group, and salts thereof.

In other embodiments, the first and/or second cross-linking agent(s) can be ionic photoactivatable cross-linking agents having the formula:

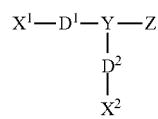

wherein $X^1$ includes a first photoreactive group; $X^2$ includes a second photoreactive group; Y includes a core molecule; Z includes at least one charged group; $D^1$ includes a first degradable linker, and $D^2$ includes a second degradable linker.

In other embodiments, the first and/or second cross-linking agent(s) can be non-ionic photoactivatable cross-linking agent having the formula $XR^1R^2R^3R^4$, where X is a non-ionic chemical backbone, and $R^1$, $R^2$, $R^3$, and $R^4$ are radicals that include a latent photoreactive group.

In other embodiments, the first and/or second cross-linking agent(s) can be non-ionic photoactivatable cross-linking agents of the formula: $PG^2$-$LE^2$-X-$LE^1$-$PG^1$, wherein $PG^1$ and $PG^2$ include, independently, one or more photoreactive groups; $LE^1$ and $LE^2$ are, independently, linking elements, including urea, carbamate, or a combination thereof; and X represents a polymeric or non-polymeric core molecule.

In other embodiments, the first and/or second cross-linking agent(s) can be non-ionic photoactivatable cross-linking agents having the general formula $R^1$—X—$R^2$, wherein $R^1$ is a radical comprising a vinyl group, X is a radical comprising from about one to about twenty carbon atoms, and $R^2$ is a radical comprising a photoreactive group.

In other embodiments, the first and/or second cross-linking agent(s) can be a compound having the structure (I):

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group In another embodiment, the first layer and/or second layer in the coating may further include an acrylamide polymer comprising at least one photoreactive group. For example, an acrylamide photo-polymer can be formed from monomer components comprising acrylamide, 2-acrylamido-2-methylpropanesulfonate (AMPS), a photogroup derivatized acrylamide monomer, and poly(ethylene glycol)-containing monomer. An exemplary acrylamide photo-polymer is N-acetylated poly[acrylamide-co-sodium-2-acrylamido-2-methylpropanesulfonate-co-N-(3-(4-benzoylbenzamido) propyl) methacrylamide]-co-methoxy-poly(ethylene glycol) monomethacrylate.

In some embodiments, the coating provides predetermined amounts of vinyl pyrrolidone polymer and acrylamide polymer. For example, the coating comprises amounts of the vinyl pyrrolidone polymer comprising a photoreactive group and the acrylamide polymer comprising a photoreactive group at a weight ratio in the range of approximately 3:1 to approximately 1:3 (wt./wt.), respectively.

In some embodiments, the coating provides predetermined amounts of vinyl pyrrolidone polymer and a first cross-linking agent. For example, the first coated layer comprises amounts of the vinyl pyrrolidone polymer comprising a photo reactive group and the first cross-linking agent comprising at least two photoreactive groups in the range of approximately 8:1 to approximately 16:1 (wt./wt.), respectively.

In some embodiments, the coating provides predetermined amounts of acid group-containing polymer (e.g., acrylic acid polymer) and acrylamide polymer. For example, the second coated layer that is the top coat has amounts of acrylic acid polymer and acrylamide polymer comprising a photoreactive group at a weight ratio in the range of approximately 2:1 to approximately 1:2 (wt./wt.), respectively.

In some embodiments, the coating provides predetermined amounts of acid group-containing polymer (e.g., acrylic acid polymer) and a second cross-linking agent. For example, the second coated layer that is the top coat has amounts of polyacrylic acid and second cross-linking agent comprising at least two photoreactive groups at a weight ratio of approximately 13:1 (wt./wt.), respectively.

In another embodiment, the disclosure includes a medical device comprising the coating comprising the first and second coating layers of the disclosure. The medical device on which the coating is formed can be made from polymers, metals, glass, ceramics, or mixtures thereof. In some embodiments, the medical device on which the coating is formed can be made from polyamide, polyimide, polyether block amide (PEBAX), polyether ether ketone (PEEK), high density polyethylene (HDPE), polyethylene, polyurethane, or polyethylene vinyl acetate.

In another embodiment, the disclosure provide a method making a medical device comprising a step of applying a base or first coating solution directly or indirectly on a medical device surface to form a first layer, the first coating solution comprising a vinyl pyrrolidone polymer, a photo reactive group, and a first solvent. The photoreactive groups can be pendent from the vinyl pyrrolidone polymer, pendent on a first cross-linking agent, or both. A step of drying the first layer and exposing it to actinic radiation is also performed. Next, a step of applying a top or second coating solution onto the first layer to form a second layer, the second coating solution comprising an acid group-containing polymer (e.g., acrylic acid polymer), and optionally including photoreactive groups, in a second solvent is performed. The method also includes a step of drying the second layer and exposing it to actinic radiation.

In some embodiments the first coating solution comprises amounts of isopropyl alcohol (IPA) and water at a volume ratio in the range of about 95% IPA:5% water to about 10% IPA:90% water. In some embodiments, the second coating solution comprises amounts of isopropyl alcohol (IPA) and water at a volume ratio in the range of about 0% IPA:100% water to about 100% IPA 0% water. In still other embodiments, the second coating solution further comprises a second cross-linking agent comprising at least two photoreactive groups.

In yet another embodiment, the disclosure provides an implantable or insertable medical device having a coating, the coating comprising an acrylic acid polymer and an extracellular matrix (ECM) protein, or a peptide that includes an active portion of an ECM protein, or another bioactive peptide (for example a thrombin inhibitor peptide, such as, but not limited to, bivalirudin). The protein or peptide is covalently bonded to the acid group-containing polymer (e.g., acrylic acid polymer), and the device further comprises a vinyl pyrrolidone polymer present in a coated layer between the acrylic acid polymer and a device surface, or present in a device material formed of a melt-extruded composition, and wherein the acrylic acid polymer is hydrogen bonded with the vinyl pyrrolidone polymer.

The device comprising the ECM protein or peptide, acrylic acid polymer, and vinyl pyrrolidone polymer, can optionally include a UV photoreactive group. For example, the UV photoreactive group can be pendent from the acid group-containing polymer (e.g., acrylic acid polymer) and/ or vinyl pyrrolidone polymer; or a first cross-linking agent, such as one comprising at least two photoreactive groups, and/or a second cross-linking agent, such as one comprising at least two photoreactive groups, can be present in the coating.

The device with the ECM protein or peptide-containing coating can be used in method for treating a subject. The protein or peptide coating can provide one or more properties selected from the group consisting of enhancing cell growth, improving hemocompatibility, and reducing infection, when the subject is treated with the device.

The protein or peptide-containing coatings according to this aspect of the disclosure have one or more of the following advantageous properties: high density of peptide/ protein coupling, ability to readily form and analyze coatings having various combinations of peptides, providing high wet lubricity and low levels of particulates along with properties conferred by the peptide/protein.

The above summary of the present disclosure is not intended to describe each discussed embodiment of the present disclosure. This is the purpose of the figures and the detailed description that follows.

BRIEF DESCRIPTION OF THE FIGURES

The disclosure may be more completely understood in connection with the following drawings, in which.

While the disclosure is susceptible to various modifications and alternative forms, specifics thereof have been shown by way of example and drawings, and will be described in detail. It should be understood, however, that the disclosure is not limited to the particular embodiments described. On the contrary, the intention is to cover modifications, equivalents, and alternatives falling within the spirit and scope of the disclosure.

DETAILED DESCRIPTION OF THE ILLUSTRATIVE EMBODIMENTS

As described above, one approach to reducing the friction between a medical device and the environment surrounding the medical device is to apply a lubricious coating onto the medical device. However, many lubricious coatings are relatively ineffective in reducing the friction between the device and the environment surrounding the device (such as an intravascular space, as one example). In addition, many lubricious coatings lack sufficient durability leading to a rapid increase in friction during the course of use. Finally, many lubricious coatings, after exposure to an aqueous environment (such as within a patient) release undesirable particulate matter.

Figure 1:
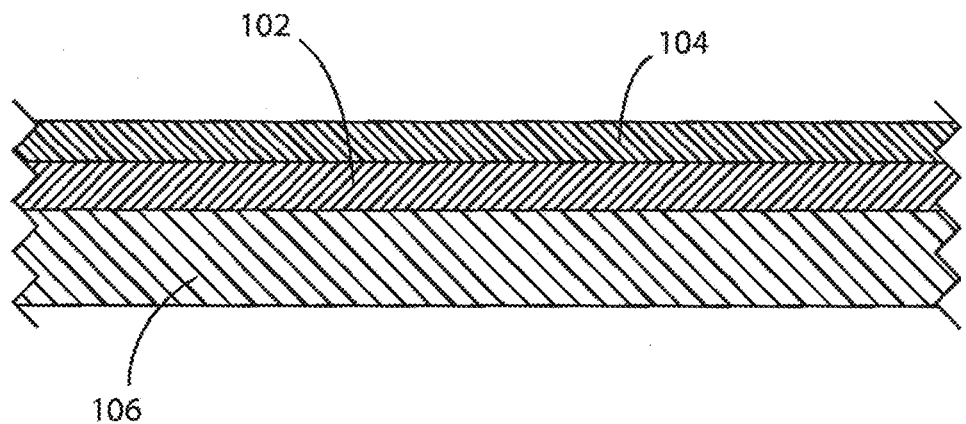
FIG. 1 is a schematic view of an embodiment of a two component coating.

Embodiments herein include coatings that are highly lubricious and that have good durability. In addition, embodiments herein include lubricious coatings that exhibit relatively low or reduced release of particulate matter. FIG. 1 is a schematic cross-sectional view of a coating on a substrate in accordance with an embodiment herein. The coating can include abase coating or first layer 102 and a top coating or second layer 104. The second layer 104 can be disposed on the first layer 102. The first layer 102 can be disposed on a substrate 106. Exemplary substrate materials are described in greater detail below. In some embodiments, the first layer 102 is directly disposed on substrate 106. In other embodiments, other components may be disposed in between the first layer 102 and the substrate 106.

The thickness of the first layer 102 and second layer 104, together, can be from about 100 nm to about 1000 nm when dry. In some embodiments, the thickness can be from about 200 nm to about 400 nm. In some embodiments, the thickness can be about 300 nm. For example, the thickness of the first coated layer, when dry, can be in the range of about 500 nm to about 5.0 μm, about 500 nm to about 2.0 μm, or about 1.0 μm to about 2.0 μm. For example, the thickness of the second coated layer, when dry, can be in the range of about 100 nm to about 5.0 μm, about 250 nm to about 5.0 μm, about 250 nm to about 1.0 μm, or about 1.0 μm to about 5.0 μm.

The coating can optionally be described in terms of the ratio of the thickness of the first vinyl pyrrolidone-containing coated layer to the second acrylic acid polymer-containing coated layer. For example, the ratio of the thickness can be in the range of about 50:1 to about 1:10 (first layer:second layer)(i.e., the first coated layer is about 50 times as thick as the second coated layer, or about one-tenth as thick as the second coated layer, or an amount in between 50× and ¹/₁₀$^{th}$), about 20:1 to about 1:2, about 10:1 to about 1:1, or about 7.5:1 to about 2.5:1.

In some embodiments, the first layer includes a vinyl pyrrolidone polymer. As used herein a "vinyl pyrrolidone polymer" refers to polymers including vinyl pyrrolidone monomeric units.

In some embodiments, coating has a first layer that includes a vinyl pyrrolidone polymer. As used herein a "vinyl pyrrolidone polymer" refers to polymers including vinyl pyrrolidone monomeric units. The vinyl pyrrolidone polymer can be a vinyl pyrrolidone homopolymer or a vinyl pyrrolidone copolymer including vinyl pyrrolidone and one or more (e.g., two, three, four, five, etc.) other monomeric units that are different than vinyl pyrrolidone. In embodiments, in a poly(vinyl pyrrolidone) copolymer, the vinyl pyrrolidone can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, vinyl pyrrolidone is present in the copolymer in the range of about 75% (mol) to about 97.5% (mol), about 85% (mol) to about 97.5% (mol), or about 90% (mol) to about 97.5% (mol).

Other monomers that can be copolymerized with vinyl pyrrolidone to provide the vinyl pyrrolidone polymer include, but are not limited to acrylamide, methacrylamide, acrylic acid, acrylamido-2-methylpropanesulfonate (AMPS), methacrylic acid, methyl acrylate, methyl methacrylate, hydroxyethyl methacrylate, hydroxyethyl acrylate, glyceryl acrylate, glyceryl methacrylate, ethylene glycol, and derivatives of these monomers.

For example, in some embodiments, the first coated layer includes a vinyl pyrrolidone polymer comprising a photoreactive group (e.g., photo-PVP). Reagents and methods for the preparation of photo-PVP can be found in references such as U.S. Pat. Nos. 4,979,959; 5,002,582; 5,263,992; 5,414,075; 5,512,329; and 5,637,460, the teaching of which are incorporated herein by reference, in some modes of practice, photo-PVP can be formed by the copolymerization of 1-vinyl-2-pyrrolidone and N-(3-aminopropyl (meth)acrylamide), which then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

A vinyl pyrrolidone polymer comprising a photoreactive group can also be prepared by copolymerizing vinyl pyrrolidone with a monomer derivatized with a photoreactive group. Exemplary monomer derivatives include aryl ketone derivatives of hydrophilic free radically polymerizable monomers such as acrylamide, methacrylamide and AMPS. One exemplary methacrylamide-based monomer with a pendent photoreactive groups is N-[3-(4-benzoylbenzamido)

propyl]methacrylamide (BBA-APMA), the synthesis which is described in Examples 1-3 of U.S. Pat. No. 5,858,653 (Duran et al.) Another exemplary methacrylamide-based monomer with a pendent photoreactive group is N-[3-(7-methyl-9-oxothioxanthene-3-carboxiamido)propyl]methacrylamide (MTA-APMA), the synthesis which is described in Examples 1-2 of U.S. Pat. No. 6,156,345 (Chudzik et al.)

Exemplary cross-linking agents comprising at least two photoreactive groups are described in greater detail herein. Within the first coated layer, the components can be homogenously mixed in some embodiments.

In some embodiments, the first coated layer comprises a first cross-linking agent comprising at least two photoreactive groups, and amounts of the vinyl pyrrolidone polymer and a firm cross-linking agent comprising at least two photoreactive groups at a weight ratio in the range of about 2:1 to about 30:1 (wt./wt.), respectively. In some embodiments, in the first coated layer the amounts of vinyl pyrrolidone polymer and the first cross-linking agent comprising at least two photoreactive groups are at a weight ratio in the range of about 2:1 to about 20:1 (wt./wt.), respectively. In some embodiments, in the first coated layer the amounts of vinyl pyrrolidone polymer and the first cross-linking agent comprising at least two photoreactive groups are at a weight ratio in the range of about 8:1 to about 20:1 (wt/wt.), respectively. In some embodiments, in the first coated layer the amounts of vinyl pyrrolidone polymer and the first cross-linking agent comprising at least two photoreactive groups are at a weight ratio in the range of about 8:1 to about 16:1 (wt./wt.), respectively. In some embodiments, in the first coated layer the amounts of vinyl pyrrolidone polymer and the first cross-linking agent comprising at least two photoreactive groups are at a weight ratio of about 18:1 (wt./wt.), respectively. In some embodiments, all components of the base coating comprise photoreactive groups.

In some embodiments, the first coated layer includes a vinyl pyrrolidone polymer without photoreactive groups (e.g., non-ionic, underivatized PVP). The underivatized PVP can be of various molecular weights. In some embodiments, the first coated layer has amounts of vinyl pyrrolidone polymer comprising a photoreactive group, non-derivatized vinyl pyrrolidone polymer, and first cross-linking agent comprising at least two photoreactive groups at a weight ratio in the range of about 8:0.1:0.1 to 13:8:1 (wt./wt/wt.), respectively. In some embodiments, the first coated layer has amounts of vinyl pyrrolidone polymer comprising a photoreactive group, non-derivatized vinyl pyrrolidone polymer, and first cross-linking agent comprising at least two photoreactive groups at a weight ratio of about 13:5:1 (wt./wt./wt.). In some embodiments, the first coated layer has amounts of non-derivatized vinyl pyrrolidone polymer and first cross-linking agent comprising at least two photoreactive groups at a weight ratio in the range of about 0.1:0.5 to 8:1 (wt./wt.), respectively.

In yet other embodiments the first coated layer can have other non-ionic exemplary polymers that include, but are not limited to, poly(N-vinyl caprolactam), polymers containing ether groups such as poly(ethylene oxide) (PEO), poly (propylene oxide) (PPO), poly(propylene glycol) (PPG) poly(vinyl methyl ether), or blends or copolymers thereof and non-ionic acrylic type polymers such as polyacrylamide, poly(N-isopropylacrylamide), and poly(N,N-dimethylacrylamide).

Other representative non-ionic exemplary polymers include, but are not limited to, polymeric alcohols such as poly(vinyl alcohol)(PVA), poly(2-hydroxyethylacrylate) (PHEA) and poly(2-hydroxyethyl vinyl ether) PHEVE, poly(2-ethyl-2-oxazoline) (PEOX), poly(n-acetyliminoethylene) (PAIE) and water soluble polysaccharides such s methyl cellulose, hydroxypropylcellulose and hydroxyethylcellulose. (see "Hydrogen-Bonded Interpolymer Complexes. Formation, Structure and Applications" Chapters 1 and 7. Eds. Vitaliy V. Khutoryanskiy and Georgios Stalkos (2009).

An "acid group-containing polymer" refers to polymer that has acid groups presented on the polymer chain. Acidic groups include, for example, sulfonic acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer are partially neutralized. For example a molar percentage of the acid groups can be neutralized with counter ions, such as in the range of x to y, wherein x to y are selected from about 1%, 5%, 10%, 15%, 20%, 25%, 30%, 40%, 50%, 60%, 70%, 80%, or 90%, wherein x is less than y.

Exemplary carboxylic acid-group containing monomers that can be used to prepare the acid group-containing polymer, include, but are not limited to acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropanesulfonic acid (AMPS), 2-(meth)acrylamido-2-methylpropane sulfonic acid, vinyl sulfonic acid, 2-sulfoethyl methacrylate, and salts thereof. Copolymers made from a combination of two or more different acid-group containing monomers can be used, or copolymers made from one or more acid-group containing monomers and one or more non-acid group containing monomers can be used. These copolymers can be random copolymers, block copolymers, graft copolymers or blends thereof to achieve the desired outcome.

Other exemplary carboxylic acid-containing monomers that can be used to prepare the acid group-containing copolymers include styrene and maleic anhydride copolymerized to produce styrene-maleic anhydride copolymer (PSMA). Yet other exemplary carboxylic acid-containing monomers are described in "Hydrogen-Bonded Interpolymer Complexes; Formation, Structure and Applications" Chapters 1 and 7, Eds. Vitaliy V. Khutoryanskiy and Georgios Stalkos (2009).

The acid group-containing polymer may optionally be described with reference to its pH. For example, the acid group-containing polymer may have a pH in the range of about 1 to about 5, about 1.2 to about 5, about 1.5 to about 5, about 2.5 to about 5, about 2.75 to about 4,3, or about 3 to about 4.25.

The second coated layer that is a top coating can comprise an acrylic acid polymer. As used herein an "acrylic acid polymer" refers to polymers including acrylic acid monomeric units. The acrylic acid polymer can be a acrylic acid homopolymer or a acrylic acid copolymer including acrylic acid and one or more (e.g., two, three, four, five, etc.) other monomeric units that are different than acrylic acid. In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 100% (mol), about 85% (mol) to about 100% (mol), about 95% (mol) to about 100% (mol), or about 98% (mol) to about 100% (mol).

In some embodiments, the acrylic acid polymer in the top coating may have an average molecular weight of 150 kDa or greater. In yet other embodiments the acrylic acid polymer in the top coating may have an average molecular weight of 250 kDa or greater, 350 kDa, 450 kDa, 550 kDa, 650 kDa or greater or even in some cases an average molecular weight of 750 kDa or greater.

In some modes of preparation, the acrylic acid polymer is prepared by free radical polymerization of acrylic acid at (e.g, about a 0.8 M concentration) in deionized water. In modes where a portion of the acid groups are neutralized, a concentrated base such as NaOH is added to the acrylic acid solution. Next, an initiator such as ammonium persulfate is added with stirring. The polymerization solution can be degassed with nitrogen and stirred for hours (e.g., 12-24 hours) at an elevated temperature (e.g., greater than 50° C.). The polymer can then be polymerized against continuous flow deionized water using 12-14 K dialysis tubing, and then isolated by lyophilization.

Figure 16:
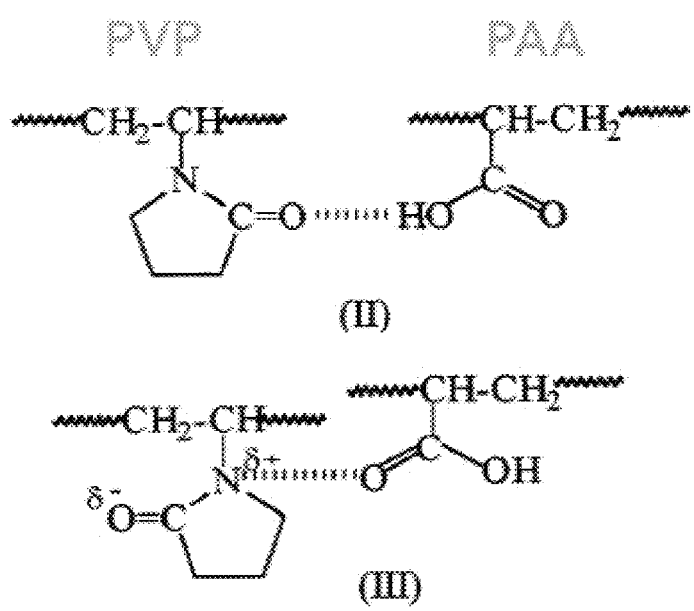
FIG. 16 is an illustration of hydrogen bonding between vinyl pyrrolidone polymer of the first coated layer and acrylic acid polymer of the second coated layer.

The acrylic acid polymer of the second layer can undergo hydrogen bonding with the vinyl pyrrolidone polymer of the first coated layer. More specifically, hydrogen bonding between the polymers can involve the carbonyl oxygens of both the pyrrolidone ring and the carboxylic acid, as shown in FIG. 16.

In other embodiments, the second coated layer that is a top coating also includes a second cross-linking agent comprising at least two photoreactive groups, or an acrylamide polymer comprising at least one photoreactive group. The second cross-linking agent may be the same or different than the first cross-linking agent. In some embodiments, the acrylamide polymer can comprise acrylamide, acrylamido-2-methylpropanesulfonate groups (AMPS), and poly(ethyleneglycol) groups. For example, in a specific embodiment, the acrylamide polymer can be N-acetylated poly[acrylamide-co-sodium-2-acrylamido-2-methylpropanesulfonate-co-N-(3-(4-benzoylbenzamido)propyl) methacrylamide]-co-methoxy poly(ethylene glycol) monomethacrylate. Reagents and method for the preparation of polymers comprising polyacrylamide in accordance with embodiments herein can be found in can be found in references such as U.S. Pat. Nos. 4,979,959; 5,002,582; 5,263,992; 5,414,075; 5,512,329; and 5,637,460, the teaching of which are incorporated herein by reference.

In some embodiments, some of the components of the second coated layer that is the top coating comprise photoreactive groups. In some embodiments, the second coated layer that is the top coating has amounts of acrylic acid polymer and acrylamide polymer at a ratio in the range of about 2:1 to about 1:2 (wt./wt.), respectively. In some embodiments, the second coated layer that is the top coating has amounts of acrylic acid polymer and second cross-linking agent comprising at least two photoreactive groups at a ratio of about 13:1 (wt./wt.). Within the second layer that is the top coating, the components can be homogenously mixed in some embodiments.

If desired, the coating can be analyzed to determine one or more coating properties. For example, the microscopy can be carried out to determine coating quality and coating thickness, in some embodiments, the coating has a thickness in the range of about 500 nm to about 10 µm, about 750 nm to about 7.5 µm, or about 1 µm to about 5 µm. Coating properties such as lubricity can be measured, as well as analysis of particulate levels.

The coating exhibits lubricity that may be observed as relative low friction. In some embodiments, the coating can be lubricious after exposure to water. The coating may exhibit lubricity of between 0 and 30 grams of force when wetted as measured by a vertical pinch test, such as that described below. In some embodiments, the coating may exhibit lubricity of less than about 20 grams of force when wetted, in some embodiments, the coating may exhibit lubricity of less than about 15 grams of force when wetted.

In various embodiments, the coating may be described in terms of durability of the lubricity. For example, the lubricity may be retained over an extended period of time when the coating is exposed to frictional forces. For example, in some embodiments, lubricity may be maintained over a plurality of frictional testing cycles. In some embodiments, the coating may exhibit a lubricity of between 0 and 30 grams of force when wetted for at least 10 consecutive testing cycles. In some embodiments, such as where at least 15 frictional test cycles are performed, the measured lubricity will increase no more than 30% between the average of cycles 1-5 and the average of cycles 10-15 of the testing.

The coating may exhibit a relatively low amount of particulate release when exposed to an aqueous environment. A description of particulate levels can be based on a predetermined coating area and thickness. In one mode of measurement the particle counts are based on 600 mm$^2$ of coated surface having a coating thickness in the range of 500 nm to 10 µm. However, it is understood that the particle count can be based on coating areas of greater or less than 600 mm$^2$. For example, the coating will generate less than 20,000 particles of greater than 10 microns in size in an aqueous environment. In some embodiments, the coating will generate less than 10,000 particles of greater than 10 microns in size in an aqueous environment. In some embodiments, the coating will generate less than 5,000 particles of greater than 10 microns in size in an aqueous environment. In some embodiments, the coating will generate less than 3.000 particles of greater than 10 microns in size in an aqueous environment. In some embodiments, the coating will generate less than 1,000 particles of greater than 10 microns in size in an aqueous environment. It will be appreciated that in accordance with various embodiments herein, the properties of lubricity and low particulate release are both present.

In some embodiments the coating has a particle count (particle sizes measured at greater than 10 µm) in the range of 500 to 10,000, in the range of 500 to 7500, in the range of 500 to 6000, in the range of 500 to 5000, in the range of 500 to 4500, in the range of 500 to 4000, in the range of 500 to 3750, in the range of 500 to 3500, in the range of 500 to 3250, or in the range of 500 to 3000, in the range of 800 to 1500, in the range of 1200 to 2000, in the range of 1500 to 3000, in the range of 2000 to 4500, in the range of 3000 to 4000, in the range of 100 to 500, or in the range of 3000 to 5000, per 600 mm$^2$ of coated surface having a coating thickness in the range of 100 nm to 10 µm.

Testing of the particulates generated in aqueous solution for the examples herein was performed according to the following procedure. As a derivative of the procedures described in ASTM F2394, substrates were passed through a tortuous path in an aqueous solution.

The coating having the first coated layer including the vinyl pyrrolidone polymer and the second coated layer including the acrylic acid polymer can have hemocompatible (blood compatible) property. For example, a medical article with a hemocompatible coating can reduce effects that may associated with placing a foreign object in contact with blood components, such as the formation of thrombus or emboli (blood clots that release and travel downstream). The hemocompatible property of the coating can be observed as compared to a medical device that does not have the coating. Optionally, the coating can be further modified with hemocompatible proteins or peptides as discussed herein to enhance the hemocompatible (blood compatible) property.

An assay for measuring hemocompatibility of a coated surface can be performed using any one of a variety of tests. Techniques, such as including clot-based tests, such an artificial circulation (Chandler loop) using whole blood augmented with platelets (e.g., see Robbie, L. A., e al. (1997) Thromb Haemost, 77:510-5), or the in-vitro bovine blood loop, chromogenic or color assays, direct chemical measurements, and ELISAs, are used for coagulation testing (e.g., see. Bates, S. M., and Weitz, J. I. (2005) *Circulation*, 112:53-60; and Walenga, J. M., et al. (2004) *Semin Thromb Hemost.* 30:683-695). Whereas clotting assays provide a global assessment of coagulation function, chromogenic tests are designed to measure the level or function of specific factors.

As used herein, the phrases "latent photoreactive group" and "photoreactive group" are used interchangeably and refer to a chemical moiety that is sufficiently stable to remain in an inactive state (i.e., ground state) under normal storage conditions but that can undergo a transformation from the inactive state to an activated state when subjected to an appropriate energy source. Unless otherwise stated, references to photoreactive groups herein shall also include the reaction products of the photoreactive groups. Photoreactive groups respond to specific applied external stimuli to undergo active specie generation with resultant covalent bonding to an adjacent chemical structure. For example, in an embodiment, a photoreactive group can be activated and can abstract a hydrogen atom from an alkyl group. A covalent bond can then form between the compound with the photoreactive group and the compound with the C—H bond. Suitable photoreactive groups are described in U.S. Pat. No. 5,002,582, the disclosure of which is incorporated herein by reference.

Photoreactive groups can be chosen to be responsive to various portions of actinic radiation. Typically, groups are chosen that can be photoactivated using either ultraviolet or visible radiation. Suitable photoreactive groups include, for example, azides, diazos, diazirines, ketones, and quinones. The photoreactive groups generate active species such as free radicals including, for example, nitrenes, carbenes, and excited states of ketones upon absorption of electromagnetic energy.

In some embodiments, the photoreactive group is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photoreactive groups include quinones such as, for example, anthraquinone.

The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source. Photoreactive aryl ketones such as benzophenone and acetophenone can undergo multiple reactivations in water and hence can provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N^3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and I-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate.

Other photoreactive groups include the diazirines (—$CHN_2$) such as 3-trifluoromethyl-3-phenyldiazirine; and ketenes (—CH=C=O) such as ketene and diphenylketene.

In particular embodiments, the photoreactive groups are aryl ketones, such as benzophenone.

Cross-linking agents used in accordance with embodiments herein can include those with at least two photoreactive groups. Exemplary cross-linking agents are described in U.S. Publ. Pat. App. No. 2011/0245367, the content of which is herein incorporated by reference in its entirety. In some embodiments, the first and/or second crosslinking agents have a molecular weight of less than about 1500 kDa. In some embodiments, the crosslinking agent can have a molecular weight of less than about 1200, 1100, 1000, 900, 800, 700,600, 500, or 400.

In some embodiments, at least one of the first and for second cross-linking agents may comprise a linking agent having formula $Photo^1$-LG-$Photo^2$, wherein $Photo^1$ and $Photo^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In some embodiments, at least one of the first and/or second cross-linking agents comprises a linking agent having a formula selected from (a):

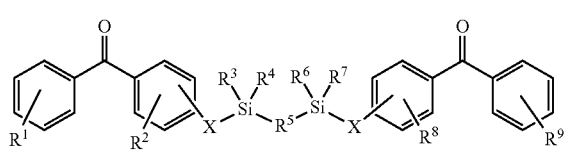

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof; (b):

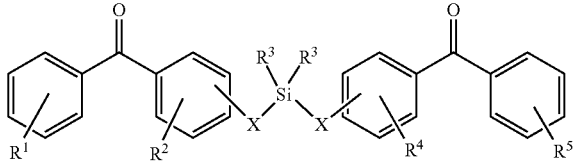

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl, or a combination thereof; (c):

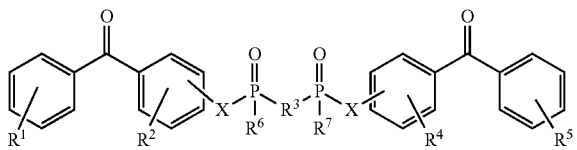

wherein $R^1$, $R^2$, $R^4$ and $R^5$ are any substitution; $R^3$ is any substitution; $R^6$ and $R^7$ are alkyl, aryl, or a combination thereof, and each X, independently, is O, N, Se, S, alkyl, or a combination thereof; and (d):

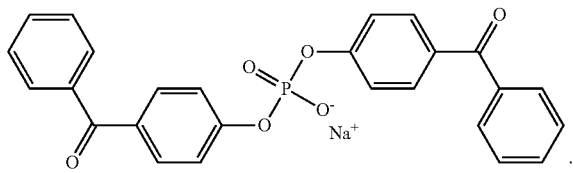

In other embodiments, the first and/or second cross-linking agent(s) can be an ionic photocrosslinking agent having good solubility in an aqueous composition, such as the first and/or second coating composition used to prepare the first layer and/or second layer. Thus, in some embodiments, at least one ionic photoactivatable cross-linking agent is used to form the coating. In some cases, an ionic photoactivatable cross-linking agent can crosslink the polymers within the second coating layer which can also improve the durability of the coating.

Any suitable ionic photoactivatable cross-linking agent can be used. In some embodiments, the ionic photoactivatable cross-linking agent is a compound of formula I: $X^1$—Y—$X^2$ where Y is a radical containing at least one acidic group, basic group, or a salt of an acidic group or basic group. $X^1$ and $X^2$ are each independently a radical containing a latent photoreactive group. The photoreactive groups can be the same as those described herein. Spacers can also be part of $X^1$ or $X^2$ along with the latent photoreactive group. In some embodiments, the latent photoreactive group includes an aryl ketone or a quinone.

The radical Y in formula I can provide desired water solubility for the ionic photoactivatable cross-linking agent. The water solubility (at room temperature and optimal pH) can be at least about 0.05 mg/mL. In some embodiments, the solubility is about 0.1 mg/mL to about 10 mg/mL or about 1 mg/mL to about 5 mg/mL.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X^1$ and $X^2$ can contain photoreactive groups such as aryl ketones. Such compounds include 4,5-bis(4-benzoylphenylmethyleneoxy)benzene-1,3-disulfonic acid or salt; 2,5-bis(4-benzoylphenylmethyleneoxy) benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate. For example, compounds of formula I can have a Y radical that contains an ammonium group; $X_1$ and $X_2$ can contain photoreactive groups that include aryl ketones. Such photoactivatable cross-linking agents include ethylenebis(4-benzoylbenzyldimethylammonium) salt; hexamethylenebis (4-benzoylbenzyldimethyl-ammonium) salt; 1,4-bis(4-benzoylbenzyl)-1,4-dimethylpiperazinediium) salt, bis(4-benzoylbenzyl) hexamethylenetetraminediium salt, bis[2-(4-benzoylbenzyl-dimethylammonio)ethyl]-4-benzoylbenzylmethylammonium salt; 4,4-bis(4-benzoylbenzyl)morpholinium salt; ethylenebis[(2-(4-benzoylbenzyldimethyl-ammonio)ethyl)-4-benzoylbenzylmethylammonium] salt; and 1,1,4,4-tetrakis (4-benzoylbenzyl)piperzinediium salt. See U.S. Pat. No. 5,714,360. The counter ion is typically a carboxylate ion or a halide. On one embodiment, the halide is bromide.

In other embodiments, the ionic photoactivatable cross-linking agent can be a compound having the formula:

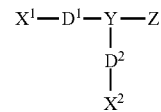

wherein $X^1$ includes a first photoreactive group; $X^2$ includes a second photoreactive group; Y includes a core molecule; Z includes at least one charged group; $D^1$ includes a first degradable linker, and $D^2$ includes a second degradable linker. Exemplary degradable ionic photoactivatable cross-linking agents are described in US Patent Application Publication US 2011/0144373 (Swan et al., "Water Soluble Degradable Crosslinker"), the disclosure of which is incorporated herein by reference.

In some aspects a non-ionic photoactivatable cross-linking agent can be used. In one embodiment, the non-ionic photoactivatable cross-linking agent has the formula $XR^1R^2R^3R^4$, where X is a non-ionic chemical backbone, and $R^1$, $R^2$, $R^3$, and $R^4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). Chemically, the first and second photoreactive groups, and respective spacers, can be the same or different.

In other embodiments, the non-ionic photoactivatable cross-linking agent can be represented by the formula: $PG^2-LE^2-X-LE^1-PG^1$, wherein $PG^1$ and $PG^2$ include, independently, one or more photoreactive groups, for example, an aryl ketone photoreactive group, including, but not limited to, aryl ketones such as acetophenone, benzophenone, anthraquinone, anthrone, anthrone-like heterocycles, their substituted derivatives or a combination thereof; $LE^1$ and $LE^2$ are, independently, linking elements, including, for example, segments that include urea, carbamate, or a combination thereof; and X represents a core molecule, which can be either polymeric or non-polymeric, including, but not limited to a hydrocarbon, including a hydrocarbon that is linear, branched, cyclic, or a combination thereof; aromatic, non-aromatic, or a combination thereof; monocyclic, polycyclic, carbocyclic, heterocyclic, or a combination thereof; benzene or a derivative thereof; or a combination thereof. Exemplary non-ionic crosslinking agents are described, for example, in U.S. application Ser. No. 13/316,030 filed Dec. 9, 2011 (Publ. No. US 2012/0149934) (Kurdyumov, "Photocrosslinker"), the disclosure of which is incorporated herein by reference.

Further embodiments of non-ionic photoactivatable cross-linking agents can include, for example, those described in U.S. Provisional Application 61/494,724 filed Jun. 8, 2011 (now U.S. application Ser. No. 13/490,994)(Swan et al., "Photo-Vinyl Primers/Crosslinkers"), the disclosure of which is incorporated herein by reference. Exemplary cross-linking agents can include non-ionic photoactivatable cross-linking agents having the general formula $R^1-X-R^2$, wherein $R^1$ is a radical comprising a vinyl group, X is a radical comprising from about one to about twenty carbon atoms, and $R^2$ is a radical comprising a photoreactive group.

Other exemplary non-ionic cross-linking agents include those formed by a mixture of the chemical backbone molecule (such as pentaerythritol) and an excess of a derivative of the photoreactive group (such as 4-bromomethylbenzophenone). An exemplary product is tetrakis(4-benzoylbenzyl ether) of pentaerythritol (tetrakis(4-benzoylphenylmethoxymethyl)methane). See U.S. Pat. Nos. 5,414,075 and 5,637,460.

A single photoactivatable cross-linking agent or any combination of photoactivatable cross-linking agents can be used in forming the coating. In sonic embodiments, at least one nonionic cross-linking agent such as tetrakis(4-benzoylbenzyl ether) of pentaerythritol can be used with at least one ionic cross-linking agent. For example, at least one non-ionic photoactivatable cross-linking agent can be used with at least one cationic photoactivatable cross-linking agent such as an ethylenebis(4-benzoylbenzyldimethylammonium) salt or at least one anionic photoactivatable cross-linking agent such as 4,5-bis(4-benzoyl-phenylmethyleneoxy)benzene-1,3-disulfonic acid or salt. In another example, at least one nonionic cross-linking agent can be used with at least one cationic cross-linking agent and at least one anionic cross-linking agent. In yet another example, a least one cationic cross-linking agent can be used with at least one anionic cross-linking agent but without a non-ionic cross-linking agent.

An exemplary cross-linking agent is disodium 4,5-bis[(4-benzoylbenzyl)oxy]-1,3-benzenedisulfonate (DBDS). This reagent can be prepared by combining 4,5-dihydroxylbenzyl-1,3-disulfonate (CHBDS) with 4-bromomethylbenzophenone (BMRP) in THF and sodium hydroxide, then refluxing and cooling the mixture followed by purification and recrystallization (also as described in U.S. Pat. No. 5,714,360, incorporated herein by reference.

A further exemplary cross-linking agent is ethylenebis (4-benzoylbenzyldimethylammonium) dibromide. This agent can be prepared as described in U.S. Pat. No. 5,714,360, the content of which is herein incorporated by reference.

Further cross-linking agents can include the cross-linking agents described in U.S. Pub). Pat. App. No. 201010274012 and U.S. Pat. No. 7,772,393 the content of all of which is herein incorporated by reference.

In some embodiments, cross-linking agents can include boron-containing linking agents including, but not limited to, the boron-containing linking agents disclosed in U.S. 61/645,903, entitled "Boron-Containing Linking Agents" by Kurdyumov, now U.S. application Ser. No. 13/866,031, and published as U.S. 201310302529, the content of which is herein incorporated by reference. By way of example, linking agents can include borate, borazine, or boronate groups and coatings and devices that incorporate such linking agents, along with related methods. In an embodiment, the linking agent includes a compound having the structure (1):

(I)

wherein $R^1$ is a radical comprising a photoreactive group; $R^2$ is selected from OH and a radical comprising a photoreactive group, an alkyl group and an aryl group; and $R^3$ is selected from OH and a radical comprising a photoreactive group. In some embodiments the bonds $B-R^1$, $B-R^2$ and $B-R^3$ can be chosen independently to be interrupted by a heteroatom, such as O, N, S, or mixtures thereof.

Additional agents for use with embodiments herein can include stilbene-based reactive compounds including, but not limited to, those disclosed in U.S. 61/736,436, entitled "Stilbene-Based Reactive Compounds, Polymeric Matrices Formed Therefrom. and Articles Visualizable by Fluorescence" now U.S. application Ser. No. 14/104,208, and published as U.S. 2014/0162083, by Kurdyumov et al, the content of which is herein incorporated by reference.

Additional photoreactive agents, cross-linking agents, hydrophilic coatings, and associated reagents are disclosed in US2011/0059874; US 2011/0046255; and US 2010/0198168, the content of all of which is herein incorporated by reference.

In some embodiments, a base or first coating solution is formed by including a vinyl pyrrolidone polymer, optionally one or more other compounds, in a solvent. For example, the solvent can comprise a vinyl pyrrolidone polymer, having a pendent photoreactive group, or the solvent can comprise a non-derivatized vinyl pyrrolidone polymer and a first crosslinking agent comprising at least two photoreactive groups. In some embodiments, the first coating solution can also include a mixture of a non-derivatized vinyl pyrrolidone polymer and a vinyl pyrrolidone polymer, having a pendent photoreactive group.

In some embodiments, the solvent for the first coating solution can include water and isopropyl alcohol (IPA). The proportion of IPA to water (vol:vol) can be in the range of about 95% IPA-5% water to about 10% IPA—90% water. For example, in some embodiments, the amount of IPA: water can a ratio of about 95:5, 90:10, 85:15, 80:20, 75:25, 70:30, 65:35, 60:40, 55:45, 50:50, 45:55, 40:60, 35:65, 30:70, 25:75, 20:80, 15:85, or 10:90 (vol:vol), or can be within a range with endpoints including any two of those ratios such that the total relative portions of IPA and water are equal to 100. In some embodiments, the solvent can include about 75% isopropyl alcohol and about 25% water.

In some embodiments, top or second coating solution is formed by including the acrylic acid polymer in a solvent. Other compound can optionally be included in the solvent. For example, the compounds can include the acrylic acid polymer, a second cross-linking agent comprising at least two photoreactive groups, a polymer comprising polyacrylamide, or a polymer derivatized with at least one photoreactive group.

In some embodiments, the solvent for the second coating solution can include water and isopropyl alcohol (IPA). The proportion of IPA to water (vol:vol) can be in the range of 0% IPA-100% water to about 60% IPA-40% water. For example in some embodiments, the amount of IPA:water can be a ratio of about (1:100, 5:95, 10:90, 15:85, 20:80, 25:75, 30:70, 35:63, 40:60, 45:55, 50:50, 55:45, 60:40 (vol:vol), or can be within a range with endpoints including any two of those ratios such that the total relative portions of IPA and water are equal to 100. In some embodiments, the solvent can include about 15% isopropyl alcohol and about 85% water.

The viscosity of the solutions can vary. In some embodiments, the viscosity of the second solution is less than about 100 centipoise (cP). In some embodiments, the viscosity of the second solution is equal to or less than about 90, 80, 70 60, 50, 40, 30, 20, or 10 cP.

The first coating solution can be applied to a substrate. Prior to application of the first coating solution to the substrate, one or more of many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON solution and sonicated. In some embodiments, a compound can be disposed on the surface of the substrate to act as a tie layer. In some embodiments the surface of the substrate can be sterilized.

Many different techniques can be used to apply the solution to the substrate. By way of example, exemplary techniques can include drop coating, blade coating, dip coating, spray coating, and the like. In various embodiments, the solution is applied by dip coating. The speed of dip coating can vary. For example, the substrate can be dipped into the base coating solution and then withdrawn at speeds between 0.01 and 10 cm/s. In some embodiments, the substrate can be dipped into the base coating solution and then withdrawn at speeds between 0.1 and 4 cm/s. In some embodiments, the substrate can be dipped into the first coating solution and then withdrawn at speeds between 0.1 and 2 cm/s. In some embodiments, the substrate can be dipped into the first coating solution and then withdrawn at speeds between 0.1 and 1.5 cm/s. In some embodiments, the substrate can be dipped into the first coating solution and then withdrawn at speeds between 0.1 and 1 cm/s. In some embodiments, the substrate can be dipped into the first coating solution and then withdrawn at speeds between 0.1 and 0.5 cm/s. In some embodiments, the substrate can be withdrawn at speeds between 0.2 and 0.4 cm/s. In some embodiments, the substrate can be withdrawn at speeds of about 0.3 cm/s.

After the first coating solution is applied to the substrate, actinic radiation such as IN radiation, can be applied to activate photoreactive groups within the components of the first coating solution forming the base layer. Actinic radiation can be provided by any suitable light source that promotes activation of the photoreactive groups. Preferred light sources (such as those available from Dymax Corp.) provide UV irradiation in the range of 190 nm to 360 nm. An exemplary UV light source is a Dymax 2000-EC series UV flood lamp with a 400 Watt metal halide bulb. A suitable dose of radiation is in the range of from about 0.5 m W/cm$^2$ to about 2.0 mW/cm$^2$. Optionally, the base coating solution can be dried, before or after application of the actinic radiation.

The second coating solution can be applied on top of the first coated layer. Many different techniques can be used to apply the solution to the substrate. In a particular embodiment, the solution is applied by dip coating. The speed of dip coating can vary. For example, the substrate can be dipped into the second coating solution and then withdrawn at speeds between 0.01 and 10 cm/s. In some embodiments, the substrate can be dipped into the second coating solution and then withdrawn at speeds between 0.1 and 4 cm/s. In some embodiments, the substrate can be dipped into the second coating solution and then withdrawn at speeds between (1.1 and 0.5 cm/s. In some embodiments, the substrate can be withdrawn at speeds between 0.2 and 0.4 cm/s. In some embodiments, the substrate can be withdrawn at speeds of about 0.3 cm/s.

In other embodiments, a coating composition including an acrylic acid polymer is applied to a device material formed by the extrusion of a composition that includes a vinyl pyrrolidone polymer and a thermoplastic, such as PEBAX. Implantable or insertable medical devices, or portions thereof, made using an extrusion process are described herein, and are also known in the art.

The coating composition applied to the extruded material may include a second cross-linking agent comprising at least two photoreactive groups, a polymer comprising polyacrylamide, or a polymer derivatized with at least one photoreactive group. In this embodiment, the extruded material containing a vinyl pyrrolidone polymer (on which the acrylic acid polymer coating is applied) can be considered a "device material" as opposed to a "first layer" or "base coat" that includes the vinyl pyrrolidone polymer, according to other embodiments of the disclosure.

In this embodiment, the coated layer including the acrylic acid polymer is directly in contact with the extruded material of the device that includes the vinyl pyrrolidone polymer and a thermoplastic. The polyacrylic acid coating on the extruded material can consist of a single coated layer including the polyacrylic acid, or can optionally include more than one coated layer, with the polyacrylic acid-containing layer present between the extruded vinyl pyrrolidone polymer/thermoplastic material of the device, and any other optional layer(s) in the coating.

The coated layer including the acrylic acid polymer can be formed on the extruded vinyl pyrrolidone polymer/ thermoplastic material of the device using one or more techniques. In some modes of practice the coating composition is applied by dip coating, such as by dip coating a device formed from extruded vinyl pyrrolidone polymer/thermoplastic polymeric material according to the dip coating techniques as described herein.

In other modes of practice, the coated layer including the acrylic acid polymer can be formed on the extruded material surface as the extruded device exits the extrusion apparatus. For example, with reference to FIG. 6, one method for preparing the coated device includes a step of extruding a composition comprising vinyl pyrrolidone polymer and a thermoplastic polymer, using extrusion equipment 60 to form all or a portion of an extruded device 62. For example, the extruded device may be in the form of a tube, or extrusion may form a thin extruded layer on the preformed tube, or a coextruded tube. The extruded device 62 includes a portion (surface) made of vinyl pyrrolidone polymer and a thermoplastic that comes into contact with the liquid solution 64 containing a polyacrylic acid (e.g., a "coating bath"). The liquid solution can provide a dual role in the process, cooling the extruded material and providing a coating bath of polyacrylic acid. The rate of movement of the extruded material through the coating bath of polyacrylic acid can be in the range as described for dip coating.

Optionally, a UV activatable photogroup can be included in the extruded composition including the vinyl pyrrolidone polymer/thermoplastic polymeric material, in the coating bath of polyacrylic acid, or both. UV activatable photogroup may be present on a crosslinking compound, pendent from a polymeric material, or both. If the device with coating is formed using a UV activatable group, also shown in FIG. 6, the extrusion and coating can be followed by a step of UV curing, where the extruded and coated device is moved through a IV irradiation area 66. A step of UV curing can be performed, for example, to promote covalent bonding via the LV activatable group, in the extruded material, the applied acrylic acid polymer-containing coating, or both.

Figure 6:
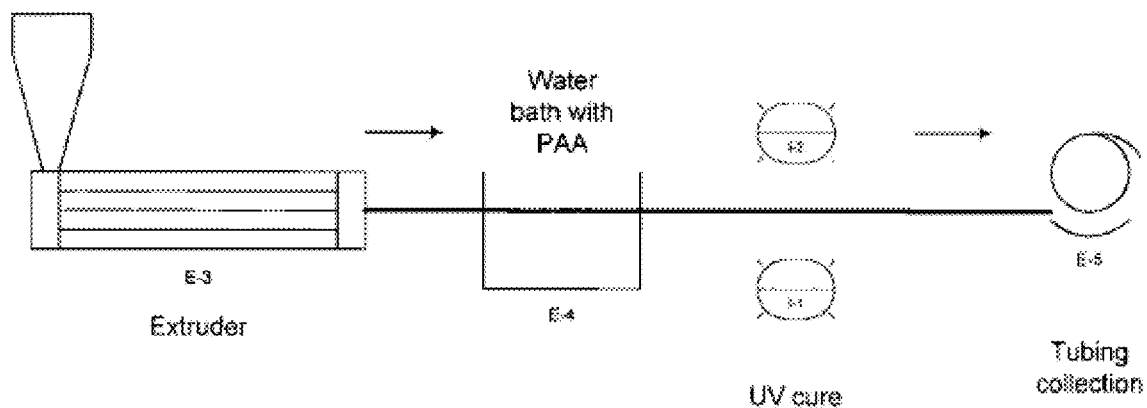
FIG. 6 is an illustration of a device forming and coating process, and equipment involved therein, including a melt extruder, coating bath, irradiation area, and winding station.

In the case where the extruded, coated device is in the form of flexible tubing, the method can optionally include an apparatus to collect the tubing, such as an automated rolling apparatus 68, illustrated in FIG. 6.

Figure 7:
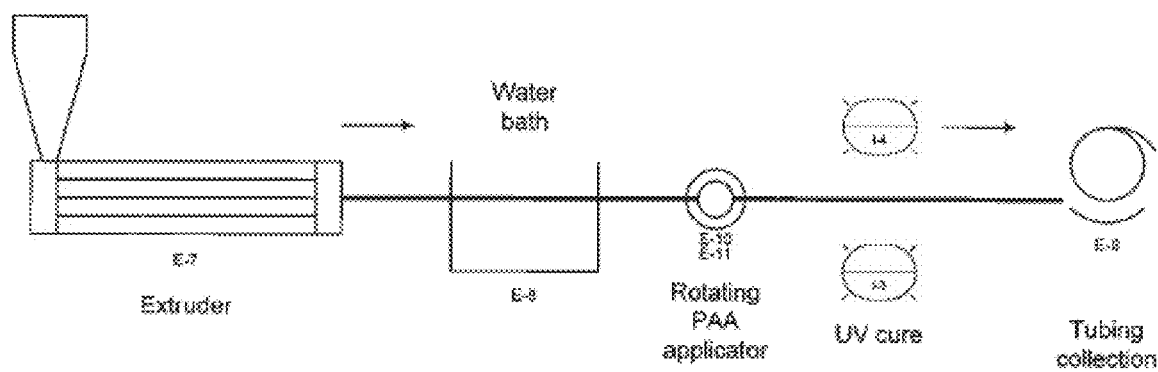
FIG. 7 is an illustration of a device forming and coating process, and equipment involved therein, including a melt extruder, cooling bath, coating area, irradiation area, and winding station.

In other modes of practice, the coating including acrylic acid polymer can be applied to the extruded material surface after the extruded device has been cooled in a water bath. For example, with reference to FIG. 7, another method for preparing the coated device includes a step of extruding a composition comprising vinyl pyrrolidone polymer and a thermoplastic using extrusion equipment 70, a step of cooling the extruded device in a water bath 74, and then a step of coating the cooled, extruded device 72 with a composition comprising acrylic acid polymer. The coating composition can be applied using an application having a rotating feature 77, such as described in U.S. Pat. No. 7,192,484 (Chappa et al.)

Optional steps of UV curing in a UV irradiation area 76 and tubing collection, using an automated rolling apparatus 78, can be performed.

In other modes of practice, one or more of the coating composition (e.g., first, second) are applied using a coating apparatus as describe in U.S. Publication No. 2013/0337147 (Chappa et al.) which describes a coating method and apparatus having a coating application unit comprising a movement restriction structure; a fluid applicator; an air nozzle; and a rotation mechanism; and an axial motion mechanism, the axial motion mechanism configured to cause movement of at least one of the coating application unit and the rotation mechanism with respect to one another.

In some mode of practice the coating includes an extracellular matrix (ECM) protein, or a peptide that includes an active portion of an ECM protein, wherein the protein or peptide is covalently bonded to acrylic acid polymer in the coating. The acrylic acid polymer is also hydrogen bonded with the vinyl pyrrolidone polymer. The vinyl pyrrolidone polymer can be present, for example, in a coated layer between the acrylic acid polymer and a device surface, or present in a device material formed of a melt-extruded composition, such as described herein.

The device comprising the ECM protein or peptide, acrylic acid polymer, and vinyl pyrrolidone polymer, can optionally include a UV photoreactive group, for example, present pendent from the acrylic acid polymer and/or vinyl pyrrolidone polymer; or present, a first cross-linking agent, such as one comprising at least two photoreactive groups, and/or a second cross-linking agent, such as one comprising at least two photoreactive groups.

As known in the art, ECM proteins provide structural support to cells and/or attach cells that reside in the ECM. Molecules on the surface of cells, such as integrins, carbohydrates, and other cell adhesion molecules can interact with ECM proteins to promote cell attachment. Exemplary ECM proteins include fibronectin, laminin, collagen, procollagen, elastin, vitronectin, tenascin, entactin, fibrinogen, thrombospondin, osteopontin (bone sialoprotein), osteocalcin, von Willibrand Factor, and active domains thereof.

An "active portion" (or "active domain") of an ECM protein refers to an amino acid sequence found within the ECM protein that, in itself, provides function according to one or more properties of the ECM protein, such as providing structural support to cells and/or for attaching cells. The active portion may also be referred to as a "domain" or "motif." The peptide that includes an active portion of an ECM protein can have a "core sequence" of amino acid residues, and optionally one or more additional amino acid residues that flank (i.e., on the C-terminus, N-terminus, or both) the core sequence. The one or more additional amino acids that flank the core sequence can correspond to the wild type ECM sequence in the relevant region of the protein, or can be an amino acid(s) that diverges from the wild type sequence (e.g., a ", variant amino acid or sequence"). The variant amino acid or sequence can be one that enhances properties of the peptide, such as providing enhanced ligand interaction, and/or can facilitate formation of the coating.

Active portions of ECM proteins are known in the art or can be determined using routine experimentation by carrying out assays that are commercially or described in a reference. For example, cell attachment assays which utilize peptides or proteins adhered to plastic or covalently immobilized on a support have been described and can be used to determine the activity of a desired peptide for promoting attachment of cells (see, for example. Malinda. K. M., et al. (1999) FASEB J. 13:53-62; or Kato, R, et al. (2006) J. Biosci. Bioeng. 101:485-95).

As used herein, a "peptide" is a short polymer of 25 or less amino acids linked by peptide bonds. As used herein, a "polypeptide" is a polymer of more than 25 amino acids linked by peptide bonds and which includes full length proteins. A peptide having an active portion of an ECM protein can be synthesized by solid phase peptide synthesis (SPPS) techniques using standard techniques, such as Fmoc synthesis. See, for example, Carpin, et al. (1970), J. Am. Chem. Soc. 92:5748-5749. Peptides described herein are also commercially available.

In some aspects, type I collagen (collagen I) can be present in the outer coated layer. Type I collagen is the most common of the collagens in vertebrates and makes up to 90% of the skeletons of the mammals, and also found in scar tissue, tendons, skin, artery walls, fibrocartilage, and bones and teeth. COL1A1 is the human gene that encodes collagen I, alpha 1 (1464 AA), with an accession reference number P02452 (CO1A1_HUMAN) in UniProtKB/Swiss-Prot. The human sequence shares at least 90% sequence identity with, at least, chimpanzee (UP10000E24950), dog (UP10000EB21D9), and cow (P02453).

Type I procollagen is similar to other fibrillar collagens and has three polypeptide chains (α-chains) which form a unique triple-helical structure. It is a heterotrimer of two α1(1) and one α2(1) chains. Among species, the α1(1) chain is more conserved than the α2(1) chain (Kimura 1983). Type I collagen molecule contains an uninterrupted triple helix of approximately 300 nm in length and 1.5 nm in diameter flanked by short nonhelical telopeptides. The helical region is highly conserved among species (Chu et al. (1984) *Nature* 310:337-340).

Collagen peptides can also be used in the coating. Such peptides include RGD, YIGSR (SEQ ID NO:1), and (GPNI) repeats (see, for example, Johnson, G. (2000) 1. Biomed. Mat. Res., 51:612-624). Collagen peptides, as well as other peptides that include a portion of an ECM protein, can be in linear or cyclic form (e.g., commercially available from Peptides International, Inc., Louisville. KY).

Recombinant collagen, such as recombinant human collagen, can optionally be used in the coating, Recombinant collagen can be expressed in single cell organisms, such as yeast, in which collagen chains are expressed from a transgenic nucleic acid sequence. Recombinant human collagen I and human collagen III are commercially available (e.g., from FibroGen. Inc. San Francisco, CA), and can be prepared from human proalpha1(I), proalpha2(I) and both alpha and beta subunits of prolyl hydroxylase genes co-expressed in *Pichia pastoris*, and converted into mature collagen (from procollagen I) by proteinase digestion. Human proalpha1 (III) can be expressed and digested in the same way to prepare mature collagen (from procollagen III).

Atelocollagen can optionally be used in the coating. Atelocollagen can be prepared by removing antigenic telopeptides at each end of a collagen I molecule using a proteolytic enzyme, such as pepsin. Removal of the telopeptides generally improve solubility of the collagen, and render it soluble in an acidic solution (e.g., in the range of about 3.0 to 4.5) Atelocollagen can be prepared from collagen from an animal source, such as from porcine tissue. Methods for the preparation of atelocollagen are known in the art (see, for example, U.S. Pat. Nos. 3,949,073 and 4,592,864) and are also commercially available under the tradename Theracol™ (Regenerative Medical Systems, Hertfordshire, UK).

Hydrolyzed collagen (also known as gelatin) can optionally be used in the coating. Gelatin is formed from the hydrolysis of collagen using heat, and/or acid or alkali solutions, and results in collagen polypeptides or peptides that have a lower molecular weight than collagen. Recombinant gelatins having sixes of 100 kDa or 8.5 kDa are commercially available (e.g., from FibroGen, Inc. San Francisco, CA).

Peptides derived from a collagen sequence can also be used in the outer coating. Exemplary collagen peptides comprise the sequences DGEA (SEQ ID NO:2), KDGEA (SEQ ID NO:3), GER, and GFOGEFR, (SEQ ID NO:4) (see, for example, Keely, P. J., and Parise, L. V. (1996) J Biol Chem. 271:26668-26676; Kotite, N. J., and Cunningham, L. W. (1986) J Biol Chem. 261:8342-8347; and Staatz, W. D., et al. (1991) J Biol Chem. 266:7363-7367).

Laminin, or an active portion thereof, can be used in the coating. The laminin protein family includes multidomain glycoproteins that are naturally found in the basal lamina. Laminins are heterotrimers of three non-identical chains: one α, β, and γ chain that associate at the carboxy-termini into a coiled-coil structure to form a heterotrimeric molecule stabilized by disulfide linkages. Each laminin chain is a multidomain protein encoded by a distinct gene. Several isoforms of each chain have been described. Different alpha, beta, and gamma chain isoforms combine to give rise to different heterotrimeric laminin isoforms. Commonly used laminins are alpha 1, beta 1 and gamma 1 (i.e., Laminin-111) and alpha 5, beta 1 and gamma 1 (i.e., Laminin-511). Laminin sequences are available in UniProtKB/Swiss-Prot, including laminin subunit alpha-1 (P25391; LAMA1_HUMAN), laminin subunit alpha-5 (O15230; LAMA5_HUMAN), laminin subunit beta-1 (P07942; LAMB1_HUMAN), and laminin subunit gamma-1 (P11047; LAMC1_HUMAN).

Peptides derived from a laminin sequence can also be used in the coating. Exemplary laminin peptides comprise the sequences LRGDN (SEQ ID NO:5) and IKVAV (SEQ ID NO:6), YFQRYLI (SEQ ID NO:7)(Laminin A), YIGSR (SEQ ID NO:1), CDPGYIGSR (SEQ ID NO:8), and PDSGR (SEQ ID NO:9) (Laminin B1), and RNIAEIIKDA (SEQ ID NO:10)(Laminin 82). Synthetic peptides based on laminin sequences also include RQVFQVAYIIIKA (SEQ ID NO: 11) and RKRLQVQLSIRT (SEQ ID NO:12) from the laminin alpha1 chain (Kikkawa, Y., et al (2009) *Biomaterials* 30:6888-95; and Nomizu, M., et al. (1995). *J Biol Chem.* 270:20583-90). The F9 peptide from the B1 chain of laminin has the sequence RYVVLPRPVCFEKK (SEQ ID NO:47).

In some aspects, the coating can include a collagen or laminin polypeptide or peptide, or a peptide comprising a RGD motif Preferred peptides are those containing RGD motifs such as the GRGDSP (SEQ ID NO:13) sequence from fibronectin as well as cell adhesive domains from collagen-I, collagen IV, and laminins I-III.

Fibronectin is a glycoprotein (~440 kDa) that binds to integrins and has roles in cell adhesion, migration, differentiation, and growth. Fibronectin has accession number P02751 (FINC_HUMAN) in UniProtKB/Swiss-Prot.

The tripeptide Arg-Gly-Asp (RGD) is found in fibronectin as well as other proteins, and can mediate cell attachment. Certain integrins recognize the ROD motif within their ligands, and binding mediates cell-cell interactions. The RGD peptide and peptides that include the RGD motif can be used in the coating. RGD-containing peptides include those having additional amino acid(s) that flank the core RGD sequence, such as RGDS (SEQ ID NO:14), RGDT (SEQ ID NO:15), GRGD (SEQ ID NO:16), GRGDS (SEQ ID NO:17), GRGDG (SEQ ID NO:18), GRGSDSP (SEQ ID NO:13), GRGDSG (SEQ ID NO:19), GRGDNP (SEQ ID NO:20). GRGDSPK (SEQ ID NO:21), GRGDSY (SEQ ID NO:22). YRGDS (SEQ ID NO:23), YRGDG (SEQ ID NO:24), YGRGD (SEQ ID NO:25). CGRGDSY (SEQ ED NO:26), CGRGDSPK (SEQ ID NO:27), YAVTGRGDS (SEQ ID NO:28), RGDSPASSKP (SEQ ID NO:29) GRGD-SPASSKG (SEQ ID NO:30). GCGYGRGDSPG (SEQ ID NO:31), GGGPHSRNGGGGGRGDG (SEQ ID NO:32). In some cases the RGD-containing peptide has one or more lipophilic amino acid residues adjacent to the aspartic acid (D), such as RGDV (SEQ ID NO:33), RGDF (SEQ ID NO:34), GRGDF (SEQ ID NO:35), GRGDY (SEQ ID NO:36), GRGDVY (SEQ ID NO:37), and GRGDYPC (SEQ ID NO:38) (Lin, H. B., et al. (1994) *J. Biomed. Mat. Rev.* 28:329-342). Peptides derived from fibronectin and that do not include an RGD motif, can also be used in the second coated layer. Other non-RGD peptides have or include sequences such as NGR, LDV, REDV (SEQ ID NO:39), EILDV (SEQ ID NO:40), or KQAGDV (SEQ ID NO:41). The fibronectin peptide WQPPRARI (SEQ ID NO:45; also known as FN-C/H-V) is derived from the 33/66 kD fragments of fibronectin, and has been shown to promote adhesion, spreading, and migration of RCE cells in a concentration-dependent manner (e.g., see Moordian, D. L., et al. (1993) Invest Ophthalmol Vis Sci. 34:153-164).

Elastin (also knows as tropoelastin) is a component of elastic fibers, and includes a high amount of hydrophobic glycine and proline amino acids. Elastin has accession number P15502 (ELN_HUMAN) in UniProtKB/Swiss-Prot. Peptides derived from an elastin sequence can also be used in the coating. Exemplary elastin peptides comprise the sequences VAPG (SEQ ID NO:42), VGVAPG (SEQ ID NO:43), VAVAPG (SEQ ID NO:44).

Osteopontin has been investigated fir its roles in bone remodeling, immune function, chemotaxis, cell activation, and apoptosis (e.g., see Mazzali, M. et al. (2002) QJM, 95:3-13). Peptides derived from an osteoponin sequence can also be used in the coating. An exemplary osteoponin peptide is SVVYGLR (SEQ ID NO:46), which has been reported to have adhesion and migration activity to endothelial cells, and expected to stimulate angiogenesis to improve some ischemic conditions (e.g., see Hamada, Y., et al. (2003) Biochem Biophys Res Commun. 310:153-157).

In some modes of preparing the coating, the ECM protein or peptide can be bonded to an acrylic acid polymer-containing layer using a covalent coupling (crosslinking) agent. The covalent coupling agent can include two or more different chemical groups that are reactive with groups on the acrylic acid polymer and ECM protein (or peptide), respectively. For example, the coupling reagent can couple carboxyl groups of the acrylic acid polymer to primary amines of the ECM protein or peptide.

In some modes of practice, the covalent coupling agent is EDC (1-Ethyl-3-[3-dimethylaminopropyl]carbodiimide hydrochloride). EDC can react with a carboxyl group on the acrylic acid polymer, forming an amine-reactive O-acylisourea intermediate. The intermediate can then with an amine on ECM protein or peptide. The EDC coupling reagent can be used in combination with a NHS (N-hydroxysulfosuccinimide) reagent, such as sulfo-NHS. The o-acylisourea ester dye intermediate creased by EDS can be replaced with the NHS group to stabilize the amine-reactive intermediate by converting it to an amine-reactive NHS ester. The amine-reactive NHS ester intermediate can allow a two-step crosslinking to be performed, allowing any carboxyl group(s) on the peptide or protein to remain unaltered.

Therefore, in some embodiments, the coating comprises an acrylic acid polymer and an ECM protein or peptide, and a coupling component covalently linking the acrylic acid polymer and ECM protein or peptide via an amide bond.

In some modes of practice, the coating including the ECM protein or peptide is formed by first providing an implantable or insertable medical device having coating comprising an acrylic acid-polymer containing layer, and including a vinyl pyrrolidone polymer present in a coated layer between the acrylic acid-polymer containing layer and a device surface, or present in a device material formed of a melt-extruded composition, and wherein the acrylic acid polymer is hydrogen bonded with the vinyl pyrolidone polymer.

A protein or peptide-containing coating composition including a coupling agent such as EDC can then be applied to a portion of, or all of, the acrylic acid polymer layer. Typically peptides and proteins contain a primary amine at the N-terminus of the molecule and occasionally contain additional primary amines if there are one or more lysine residues. Therefore amine-reactive chemistries can be used to immobilize any bioactive protein or peptide of interest which might have therapeutic benefit. Exemplary protein or peptide-containing coating compositions can include protein or peptide at a desired concentration, such as in the range of about 0.1 mg/mL to about 5 mg/mL, or about 0.25 mg/mL to about 1 mg/mL. The coating composition can also include the coupling agent, such as EDC, at a desired concentration. Unreacted protein or peptide can be washed from the surface of the device.

Figure 12:
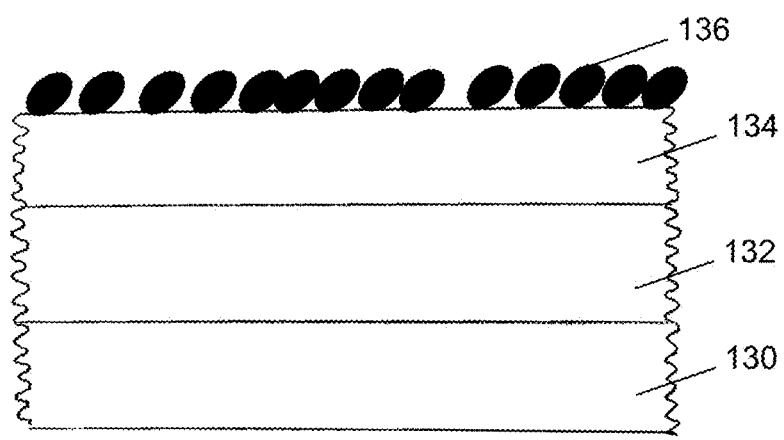
FIG. 12 a cross-sectional illustration of a portion of a coating having peptides covalently immobilized on an acrylic acid polymer-containing layer.

FIG. 12 shows a coating embodiment with a device portion having a device surface 130, a vinyl pyrrolidone polymer-containing base layer 132, a acrylic acid polymer-containing layer 134, and peptide molecules 136, present at a high density on the layer 134, covalently bonded to the acrylic acid polymer in layer 134.

Protein and peptides that provide improved hemocompatibility can be coupled to the surface of the coating. Hemocompatibility molecules can act by inhibiting proteins involved in the coagulation cascade. An exemplary hemocompatibility protein is antithrombin III which specifically inhibits the activity of thrombin which is the final protein involved in the coagulation cascade and responsible for generating an insoluble fibrin clot. Other exemplary hemocompatibility proteins are anti-thrombin antibodies that can target and inhibit thrombin activity. Other exemplary hemocompatibility proteins include but are not limited to thrombomodulin (an endothelial glycoprotein with potent anticoagulant activity). Another exemplary hemocompatibility protein that inhibits coagulation is corn trypsin inhibitor, a small protein isolated from corn which inhibits Factor XIIa the trigger of the intrinsic coagulation cascade. Several peptides are also known that inhibit thrombin either directly or indirectly. For example, hirudin is a peptide derived from leaches which directly inhibits thrombin activity. Bivalirudin is a short synthetic peptide based on hirudin which also possesses potent thrombin-inhibitory activity and is used therapeutically as an anti-coagulant. Other peptide inhibitors of thrombin are known including s-variegin and other variants based on its sequence as described in Koh. C. Y. et al. (2011) *PLOS One*. 6(10):e26367. Other known thrombin inhibitors include peptide chloromethylketones such D-phenylalanyl-L-prolyl-L-arginine chloromethyl ketone (PPACK) and Glu-Gly-Arg-chloromethyl ketone (GGACK) which are commercially available from Haematologic Technologies, Inc. (Essex Junction, VT).

The coating can exhibit reduced platelet accumulation, the reduction being greater than 20% of the control, greater than 30% of the control, greater than 40% of the control, greater than 50% of the control, greater than 60% of the control, or greater than 70% of the control, or (b) reduced fibrin accumulation, the reduction being greater than 25% of the control, greater than 50% of the control, greater than 60% of the control, greater than 70% of the control, greater than 80% of the control, or greater than 90% of the control, or both (a) and (b).

Substrates on which the coating can be formed can be partially or entirely fabricated from a metal, ceramic, glass, or the like, or a combination thereof. Substrates can include polymers such as polyurethanes and polyurethane copolymers, polyethylene, polyolefins, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyester, polyvinyl chloride, polyether-polyester copolymers, polyether-polyamide copolymers, and the like. The substrate can be made of a single material or a combination of materials.

Substrate polymers can also include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

In some embodiments, the substrate includes a polymer selected from the group consisting of polyamide, polyimide, polyether block amide (PEBAX), polyether ether ketone (PEEK), high density polyethylene (HDPE), polyethylene, polyurethane, and polyethylene vinyl acetate.

Metals that can be used as substrates in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, nonferrous alloys, and platinum/iridium alloys. One exemplary alloy is MP35.

In some embodiments the substrate, or a portion of the substrate, is formed by melt extruding a thermoplastic elastomer with a vinyl pyrrolidone polymer. A "thermoplastic elastomer" (or a "thermoplastic rubber") refers to a rubber-like material that can be processed like thermoplastic materials. Thermoplastic elastomers include copolymers and polymer blends, including those specifically described herein, having elastomeric and thermoplastic properties. Thermoplastic elastomers include styrene-based block copolymers, polyolefin polymers, thermoplastic polyurethanes, thermoplastic copolyesters, and thermoplastic polyamides, such as polyether block amide (PEBAX) polymers.

Melt extrusion can be carried out by combining raw polymeric materials including a thermoplastic elastomer, such as PEBAX, and a vinyl pyrrolidone polymer, such as poly(vinyl pyrrolidone) (PVP). In some modes of practice, the extrusion uses a mixture of having an amount of vinyl pyrrolidone polymer that is lower than the amount of the thermoplastic elastomer (e.g., a low PVP/PEBAX ratio). For example, in some embodiments the vinyl pyrrolidone polymer is present in the extrusion composition in an amount of about 45% (wt) or less, about 40% (wt) or less, about 35% (wt) or less, or about 30% (wt) or less; such as in the range of about 5% (wt) to about 45% (wt), or about 10% (wt) to about 40% (wt). In some embodiments the thermoplastic elastomer, such as PEBAX, is present in the extrusion composition in an amount of about 55% (wt) or greater, about 60% (W) or greater, about 65% (wt) or greater, or about 70% (wt) or greater; such as in the range of about 55% (wt) to about 95% (wt), or about 60% (wt) to about 90% (wt).

Melt extrusion of the polymeric materials can be performed using methods and melt extrusion equipment known in the art. For example, the polymeric starting materials, such as in the form of pellets or granules, can be ed into feeders which provide the pellets/granules into a mixing barrel having one or more heat zone(s). The melt extruder can include a screw for the heating and mixing of prior to extrusion through the die. Melt extrusion processes, such as described in WO07/081603 can be used in method for forming the medical device.

Figure 8:
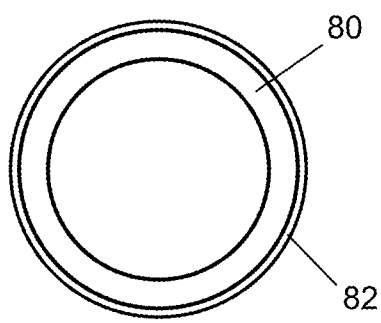
FIG. 8 is a cross-sectional illustration of an extruded tubular device (end view), the device having a coating on its outer surface.
Figure 9:
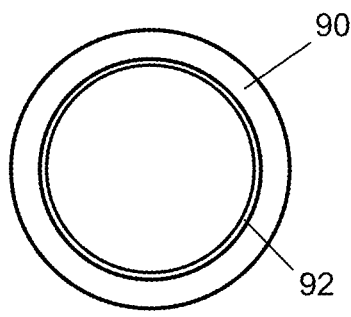
FIG. 9 is a cross-sectional illustration of an extruded tubular device (end view), the device having a coating on its inner surface.

In some embodiments, the melt extruded polymeric materials forms most or all of the device material. For example, melt extruded PVP/PEBAX can form a conduit, such as tubing that can be a part of a catheter assembly as described herein or those known in the art. The melt extruded PVP/PEBAX can then be coated with a composition that includes an acrylic acid polymer on the outer surface, inner surface, or both outer and inner surfaces using techniques as described herein. FIG. 8 shows an embodiment with a melt extruded tube 80 formed of PVP/PEBAX, and a coating 82 including an acrylic acid polymer on the outer surface of the tube. FIG. 9 shows an embodiment with a melt extruded tube 90 formed of PVP/PEBAX, and a coating 92 including an acrylic acid polymer on the inner surface of the tube.

In other cases, melt extruded PVP/PEBAX can form a portion of the medical device, with the coating that includes the an acrylic acid polymer in contact with the PVP/PEBAX portion. For example, the PVP/PEBAX can form a first portion of the device in contact with the coating, and the device can include a second portion, etc., that is a distinct portion of the device made from a different material, or different material combination.

In some modes of construction, the extruded PVP/PEBAX is present as a first portion of the device that is formed by extrusion on another (e.g., second) portion of the device. The second portion of the device can be made from another thermoplastic, or made from a metal. The second portion of the device can be formed into a desired shape or configuration prior to extruding the PVP/PEBAX on the second portion.

In other modes of construction, the PVP/PEBAX can be co-extruded with a different thermoplastic, or different thermoplastic combination, so the PVP/PEBAX forms a first portion of the device, and the different thermoplastic forms a second portion of the device. For example. PVP/PEBAX can be co-extruded with a nylon or PTFE.

Figure 10:
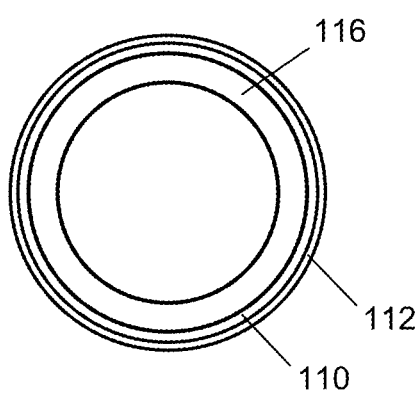
FIG. 10 is a cross-sectional illustration of a tubular device (cud view), the having an intermediate extruded layer and coating on its outer surface.
Figure 11:
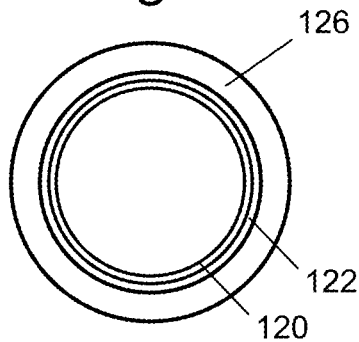
FIG. 11 a cross-sectional illustration of a tubular device (end view), the having an intermediate extruded layer and coating on its inner surface.

In some constructions the PVP/PEBAX is extruded as a thin layer (first portion) on a second portion of the device that substantially thicker than the first portion. For example, the PVP/PEBAX is extruded as a thin layer on the inner surface, outer surface, or both inner and outer surface of the second portion of the device which is a tube made from a different thermoplastic, such as nylon or PTFE, or metal. The melt extruded PVP/PEBAX forming the thin layer can then be coated with a composition that includes the acrylic acid polymer using techniques as described herein. FIG. 10 shows an embodiment with a tube 116 formed of a thermoplastic or metal material, a thin PVP/PEBAX layer 110 on the outer surface of the tube, and a coating 112 including an acrylic acid polymer on the PVP/PEBAX layer. Figure 11 shows an embodiment with a tube 126 formed of a thermoplastic or metal material, a thin PVP/PEBAX layer 120 on the inner surface of the tube, and a coating 122 including an acrylic acid polymer on the PVP/PEBAX layer.

Optionally, a UV activatable photogroup can be included in the extruded PVP/PEBAX device (e.g., 80 or 90 of FIGS. 8 and 9, respectively), extruded PVP/PEBAX layer (e.g., 110 or 120 of FIGS. 10 and 11, respectively), acrylic acid polymer-containing coating (e.g., 82, 92, 112, or 122 of FIGS. 8, 9, 10, or 11 respectively), or combinations thereof. The UV activatable photogroup may be present on a cross-linking compound, pendent from a polymeric material, or both.

The methods and materials of the disclosure can be utilized to coat virtually any medical device for which it is desired to provide a hydrophilic and lubricious coating on a surface. In particular, the coatings are particularly useful for medical articles that can be inserted into and moved within the body.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PF) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff; sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products, vena cava filters, and embolic protection filters and devices and electrophysiology mapping and ablation catheters.

In some embodiments coatings of the present disclosure can be used on exemplary medical devices such as braided catheters. In yet other embodiments the coatings can be used advantageously on braided catheters (e.g. PEBAXN®).

Figure 2:
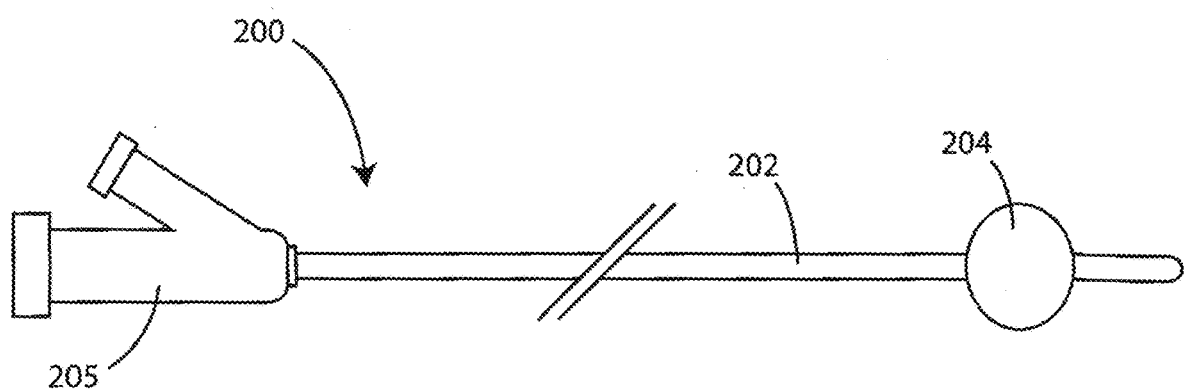
FIG. 2 is a schematic view of an embodiment of a coated medical device.

FIG. 2 is a schematic view of an exemplary device is shown in accordance with a specific embodiment. The device 200 can be, for example, a catheter, such as an angioplasty balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. The device 200 includes a catheter shaft 202 and a manifold end 205. The device 200 also includes an inflatable balloon 204 disposed around the catheter shaft 202. In FIG. 2, the balloon 204 is shown in an inflated configuration. The catheter shaft 202 can include a channel to convey air through the catheter shaft 202 and to or from the balloon 204, so that the balloon 204 can selectively go from a deflated configuration to the inflated configuration and back again. The catheter shaft, and/or the balloon, can have a coating, such as those described herein, disposed thereon.

The present disclosure may be better understood with reference to the following examples. These examples are intended to be representative of specific embodiments of the disclosure, and are not intended as limiting the scope of the disclosure.

EXAMPLES

The following reagents, coating solutions, and substrates were used in generating the examples.

PA-BBA-AIMPS-PEG

N-Acetylated poly[acrylamide$^{93.6\%}$-co-sodium-2-acrylamido-2-methylpropanesulfonate$^{4.9\%}$-co-N-(3-(4-benzoylbenzamido)propyl) methacrylamide$^{0.9\%}$]-co-methoxy poly (ethylene glycol)$_{1000}$ monomethacrylate$^{0.6\%}$ (percentages are mole percents) was obtained (PA-BBA-AMPS-PEG). Reagents and methods for the preparation of PA-BBA-AMPS-PEG can be found in references such as U.S. Pat. Nos. 4,979,959; 5,002,582; 5,263,992; 5,414,075, 5,512,329; and 5,637,460, the teaching of which are incorporated herein by reference.

Photo-PVP

Polyvinylpyrrolidone having an average molecular weight of about 1,450 kDa with benzophenone photoreactive groups was prepared according to the methods described in U.S. Pat. No. 5,637,460.

BPP

The cross-linking agent sodium bis(4-benzoylphenyl) phosphate was prepared according to the methods described in U.S. Pub. No. 2012/0046384.

PAA

Poly(acrylic acid) having an average molecular weight of 450 kDa was obtained from Sigma-Aldrich.

PVP-K30

PVP-K30 having an average molecular weight of 50 kDa was obtained from BASF.

Coating Solution A

A coating solution was prepared by mixing together Photo-PVP at 18 g/L; and BPP at 1 g/L in a solvent of 75% isopropyl alcohol and 25% water.

Coating Solution B

A coating solution was prepared by mixing together Photo-PVP at 10.5 g/L; PA-RBA-AMPS-PEG at 10.5 g/L; BPP at 0.1 g/L in a solvent of 15% isopropyl alcohol and 85% water.

Coating Solution C

A coating solution was prepared by mixing together PAA at 10.5 g/L; PA-BBA-AMPS-PEG at 10.5 g/L; BPP at 0.1 g/L in a solvent of 15% isopropyl alcohol and 85% water.

Coating Solution D

A coating solution was prepared by dissolving PAA at 20 g/L in a solvent of 15% isopropyl alcohol and 85% water.

Coating Solution E

A coating solution was prepared by dissolving PVP-K30 at 20 g/L in a solvent of 15% isopropyl alcohol and 85% water.

Test Substrates

Test substrates included 40D PEBAX® braided catheter material with 30% barium sulfate (O.D. of 0.105", 40 PPI) obtained from Minnesota MedTec. Maple Grove, MN;

PEBAX® rods (O.D. 0.039"; 72D) obtained from Medicine Lake Extrusion, Plymouth. MN; and polyurethane catheters (O.D. 0.92"; catalog No. PU-C70) obtained from Solomon Scientific. San Antonio, TX.

Friction (Lubricity) and Durability Testing Method

The coated substrates of the examples were evaluated for lubricity/durability by friction measurements using a Vertical Pinch Method, as described in International Application Number WO 03/055611 with the following modifications. The coated substrate samples were hydrated in phosphate-buffered saline (PBS, pH 7.4) for ≥1 minute and then inserted into the end of a rod holder, which was placed between the two jaws of a pinch tester and immersed in a cylinder of PBS. The jaws of the pinch tester were closed as the sample was pulled in a vertical direction for 10 cm at a travel rate of 1 cm/sec and opened when the coated sample was returned to the original position. A 500 g force was applied as the coated substrates were pulled up through the pinched jaws. The pull force exerted on the substrate was then measured (grams). Pull force (g) is equal to the coefficient of friction (COF) multiplied by pinch force (g). The apparatus used for the vertical pinch test method is described in U.S. Pat. No. 7,348,055, the content of which is herein incorporated by reference.

Particulate Testing Method

Testing of the particulates generated in aqueous solution for the examples herein was performed according to the following procedure. As a derivative of the procedures described in ASTM F2394, substrates were passed through a tortuous path in an aqueous solution described as follows. The distal portion of a 6 French guide catheter (Vista Brite Tip, Cordis) was cut off and discarded so that the catheter was 30 cm long. The guide catheter was inserted into the ASTM F2394-07 model. A hemostasis valve connector (Qosina) was attached to the guide catheter. The model was cleaned by flushing 120 ml. Isoton (Becton, Dickinson, and Company) using a 60 mL syringe and discarding the flush. A base line flush with 60 mL Isoton was analyzed by light obscuration to determine background level of particulates. 60-cm rods (1 mm diameter) with 20 cm coated were hydrated in Isoton for ≥1 minute. The rods were inserted into the guide catheter and advanced until the distal portion of the rod exited the model. A 30 mL flush with Isoton was performed and collected in a glass beaker. The rod was removed and an additional 30 mL flush with Isoton was performed and collected into the same glass beaker. The collected Isoton was immediately analyzed by light obscuration for particulates ≥10 microns. The model was cleaned with 120 mL Isoton and the next coated rod was tested.

Example 1:—PVP/PAA Coating Interaction—Staining with Toludine Blue

Photo-PVP solution (20 g/L water) was added to PAA solution (40 g/L water), Upon mixing the solutions the preparation formed a gel. This demonstrated there is an interaction between these photo-PVP and PAA solutions.

A polyurethane catheter previously dip coated with photo-PVP (20 g/L water) and UV cured was then dip coated with PAA (20 g/L in water). The PAA layer was not UV cured and not allowed to dry. The coated catheter was immediately rinsed in deionized water and stained with toludine blue by holding the coated catheter in 0.1% w/v toluidine blue water solution for 1 minute and then thoroughly rinsing the sample with deionized water to remove excess stain. The coated catheter stained dark purple, indicating a strong presence of PAA in the coating.

An uncoated polyurethane catheter as described above was dip coated with PAA. The PAA layer was not IN cured and not allowed to dry. The coated catheter was immediately rinsed in deionized water and stained with toludine blue as described above. The coated catheter stained very faint blue, indicating only a minor presence of PAA remaining in the coating.

Example 2: Replacing Photo-PVP in Top Coat with PAA

Figure 3:
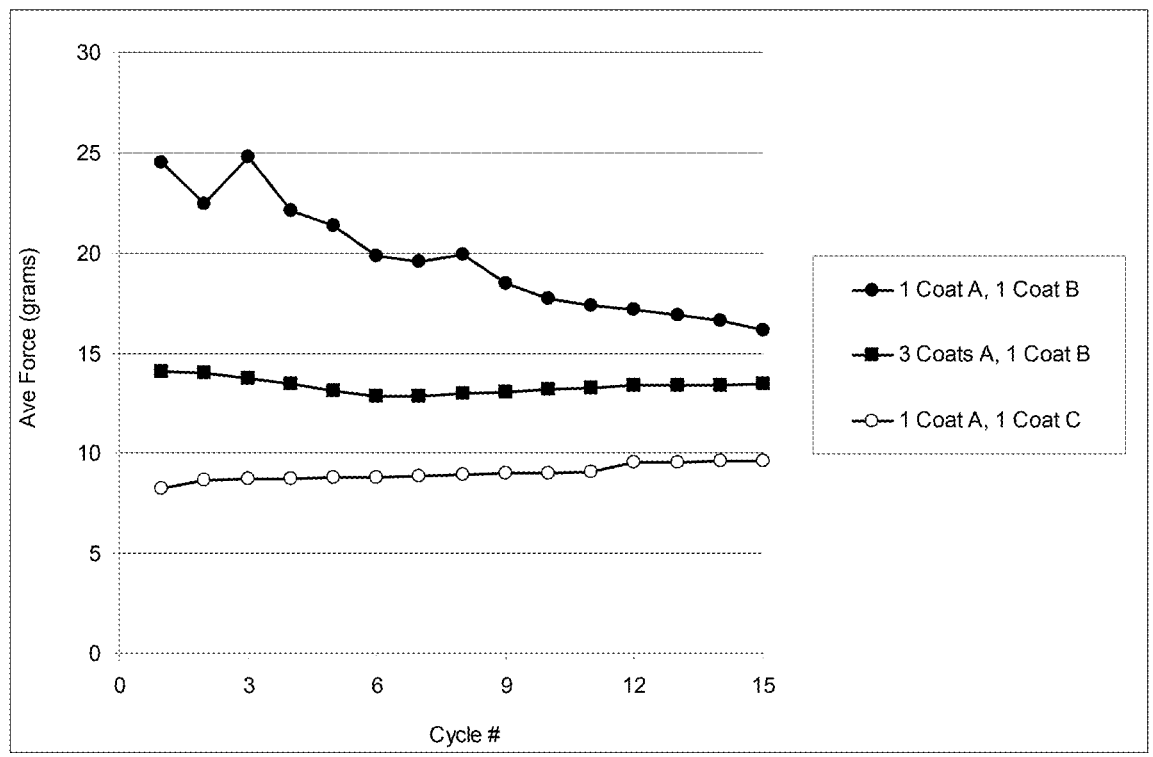
FIG. 3 is a graph of the average measured frictional force in a vertical pinch test vs. the number of testing cycles for various embodiments of the present disclosure.

Coatings were applied to PEBAX® braided catheter material (40D, 40 PPI, 30% BaSO$_4$). Specifically, coating solution A was applied as a base coat to the substrate using a dip coat method. The substrate was immersed in the coating solution A with a dwell time of 5 seconds. The substrate was then extracted from the solution at a speed of 1.5 cm/s. The base layer was then air dried for at least 10 minutes, then UV cured by rotating the coated substrate in front of a Dymax 2000-EC series IV flood lamp with a 400 Watt metal halide bulb for 30 seconds, approximately 20 cm from the light source. In one case, the base coat layer application was repeated for a total of three coats. Next, a layer of coating solution B or coating solution C was applied to the base coat layer, also by dip coating at a speed of 0.3 cm/s to form the second layer. The second layer was then air dried and UV cured using the same conditions as for the base coat layer. The friction of the coatings was then tested according to the testing procedure outlined above. The results are shown in FIG. 3.

The particulate generation of the coating was then tested according to the testing procedure outlined above. The 1 Coat A, 1 Coat B coating generated an average of 4,441 particulates ≥10 microns per rod whereas the 1 Coat A, 1 Coat C coating generated an average of 2,801 particulates ≥10 microns per rod.

Example 3: PAA Top Coat Versus PVP Top Coat

Figure 4:
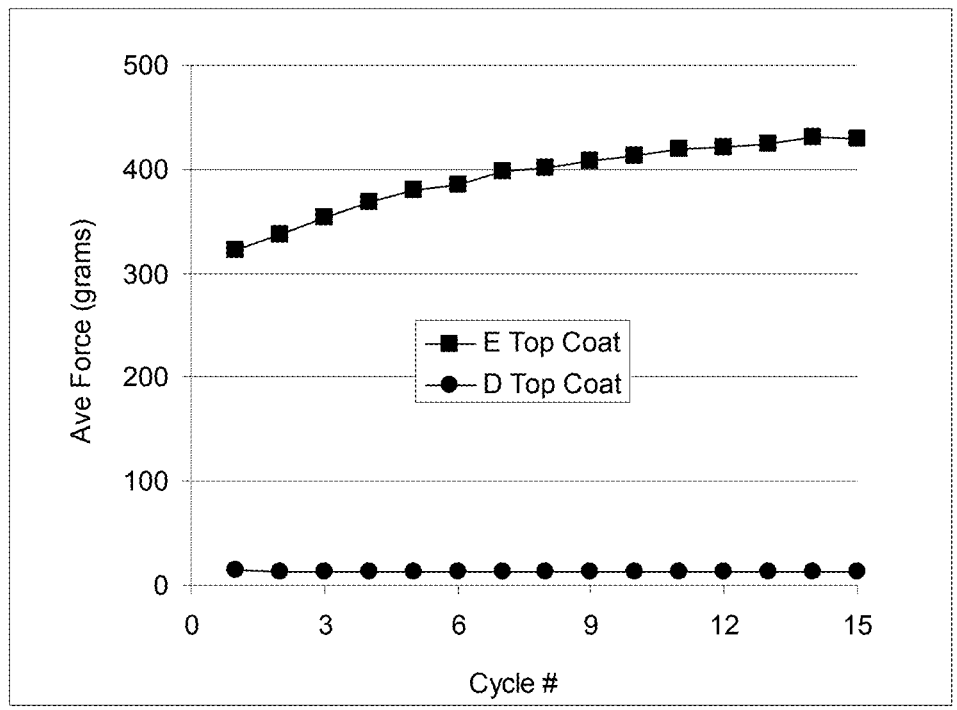
FIG. 4 is a graph of the average measured frictional force in a vertical pinch test vs. the number of testing cycles for various embodiments of the present disclosure.

Coatings were applied to PEBAX braided catheter material (40D, 40 PPI. 30% BaSO$_4$). Specifically, coating solution A was applied as a base coat to the substrate using a dip coat method. The substrate was immersed in the base coat coating solution with a dwell time of 5 seconds. The substrate was then extracted from the solution at a speed of 1.5 cm/s. The base layer was then air dried for at least 10 minutes. The base layer was then UV cured. Specifically, the coated substrate was rotated in front of a Dymax 2000-EC series UV flood lamp with a 400 Watt metal halide bulb for 30 seconds, approximately 20 cm from the light source. Next, a layer of coating solution D or coating solution E was applied to the base coal layer, also by dip coating at a speed of 0.3 cm/s to form the second layer. The second layer was then air dried and UV cured using the same conditions as for the base coat layer. The friction of the coatings was then tested according to the testing procedure outlined above. The results are shown in FIG. 4.

Example 4: Top Coat UV Cure Versus No UV Cure

Figure 5:
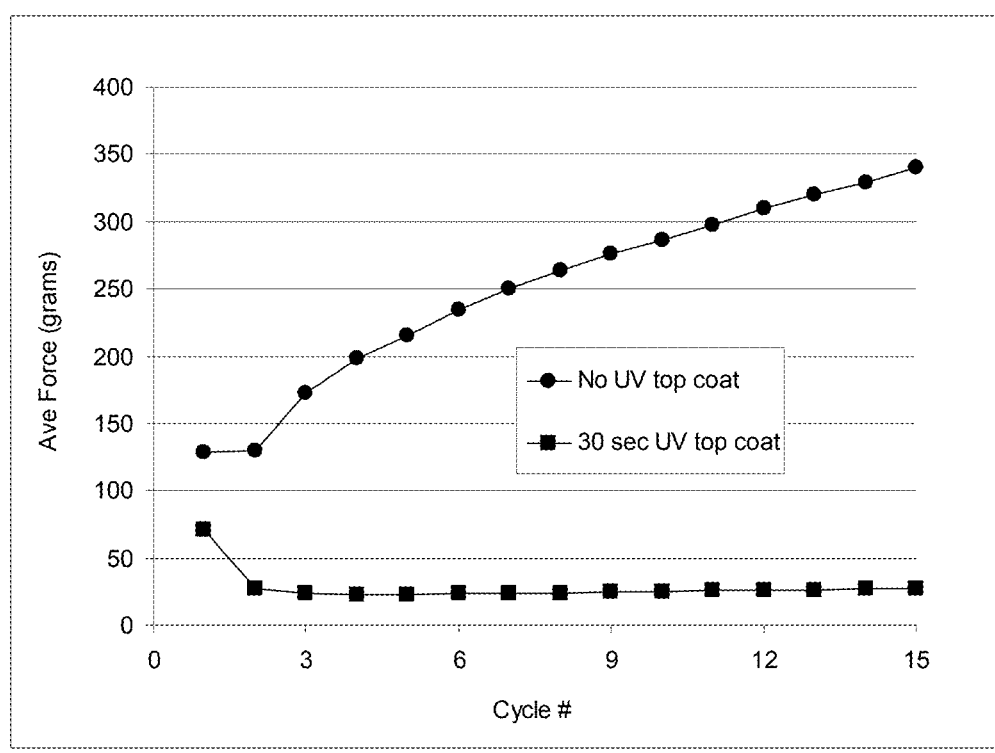
FIG. 5 is a graph of the average measured frictional force in a vertical pinch test vs. the number of testing cycles comparing no UV top coating against a 30 sec UV top coating.

Coatings were applied to PEBAX® braided catheter material (40D, 40 PPI, 30% BaSO$_4$). Specifically, coating solution A was applied as a base coat to the substrate using a dip coat method. The substrate was immersed in the base coat coating solution with a dwell time of 5 seconds. The substrate was then extracted from the solution at a speed of 1.5 cm/s. The base layer was then air dried for at least 10 minutes. The base layer was then UV cured. Specifically, the coated substrate was rotated in front of a Dymax 2000-EC series UV flood lamp with a 400 Watt metal halide bulb for 30 seconds, approximately 20 cm from the light source. Next, a layer of coating solution D was applied to the base coat layer, also by dip coating at a speed of 0.3 cm/s to form the second layer. The second layer was then air dried on all rods. One set of rods received a 30 second UV cure while the other set of rods were not UV cured. The friction of the coating was then tested according to the testing procedure outlined above. The results are shown in FIG. 5.

Example 5: PAA Peptide Coating

PEBAX 6333 SA01 sheets of 0.5 mm thickness were obtained from Specialty Extrusions, Inc (Royersford, PA). Peptides of amino acid sequence CKKRGDSP, GWQP-PRARI, GYIGSR, GIKVAV, and GSVVYGLR were synthesized at 95% purity at BioBasic, Inc. (Amherst, NY). PEBAX sheets were cut into 1×8 cm strips prior to coating. PEBAX strips were dipped in coating solution A and then removed at a rate of 1.5 cm/s. They were allowed to dry for 10 minutes and then exposed to UV for 30 seconds. Strips were then dipped in coating solution D and removed at a rate of 0.3 cm/s, dried for 10 minutes and exposed to UV for 30 s. 2-(N-morpholino)ethanesulfonic acid (Sigma-Aldrich. Saint Loiuis, MO) was dissolved in water at 0.1 M (19.5 g in 1 L) and pH was adjusted to 6.0 to prepare MES buffer. 1-Ethyl-3-[3-dimethylaminopropyl]carbodiimide (EDC) hydrochloride and N-hydroxysuccinimide (NHS) were both from Thermo Scientific (Rockford, IL). EDC and NHS were dissolved in MES buffer at a concentration of 1 mg/ml of each component. Peptides were then dissolved in MES buffer at 1 mg/ml using MES buffer containing EDC and NIS or MES buffer alone. MES buffer with peptide with and without EDC/NHS was incubated with PAA coated PEBAX strips overnight at room temperature with shaking. After overnight shaking, PEBAX strips were rinsed three times in phosphate buffered saline containing 0.05% Tween-20 followed by a rinse in water. They were then allowed to dry. Strips were sterilized by a 30 second exposure to UV light prior to cell attachment testing.

Example 6: PAA Peptide Endothelial Cell Attachment Assay

Figure 13A:
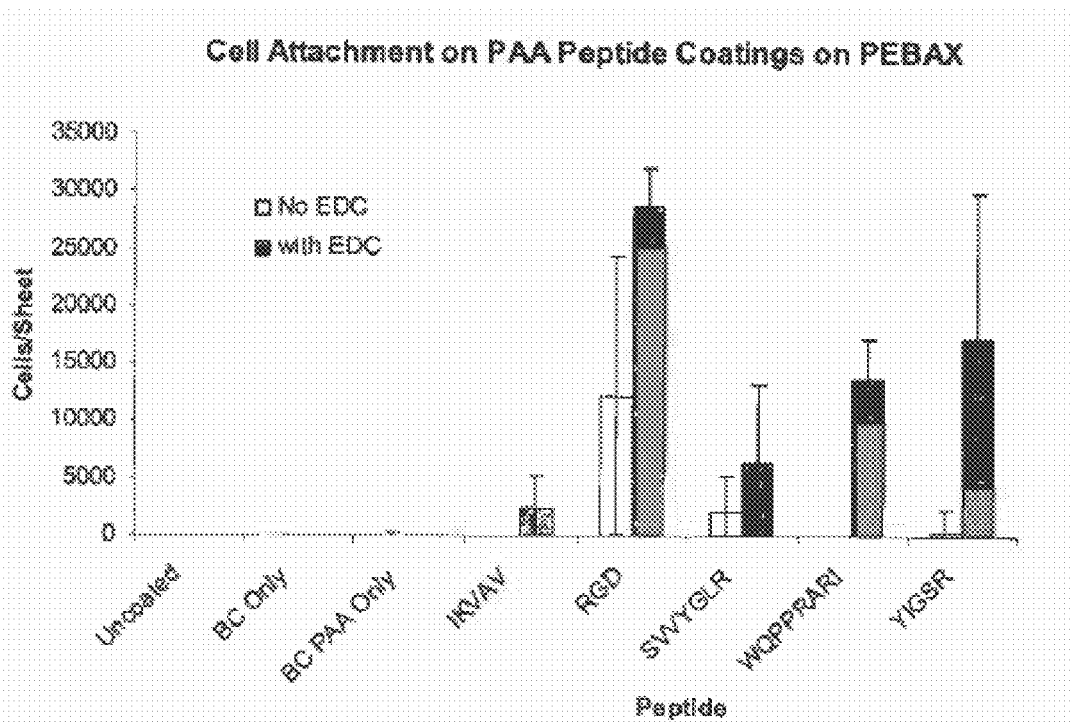
FIGS. 13A and 13B are graphs reflecting cell attachment on acrylic acid-polymer containing coatings having various peptides immobilized thereon.
Figure 13B:
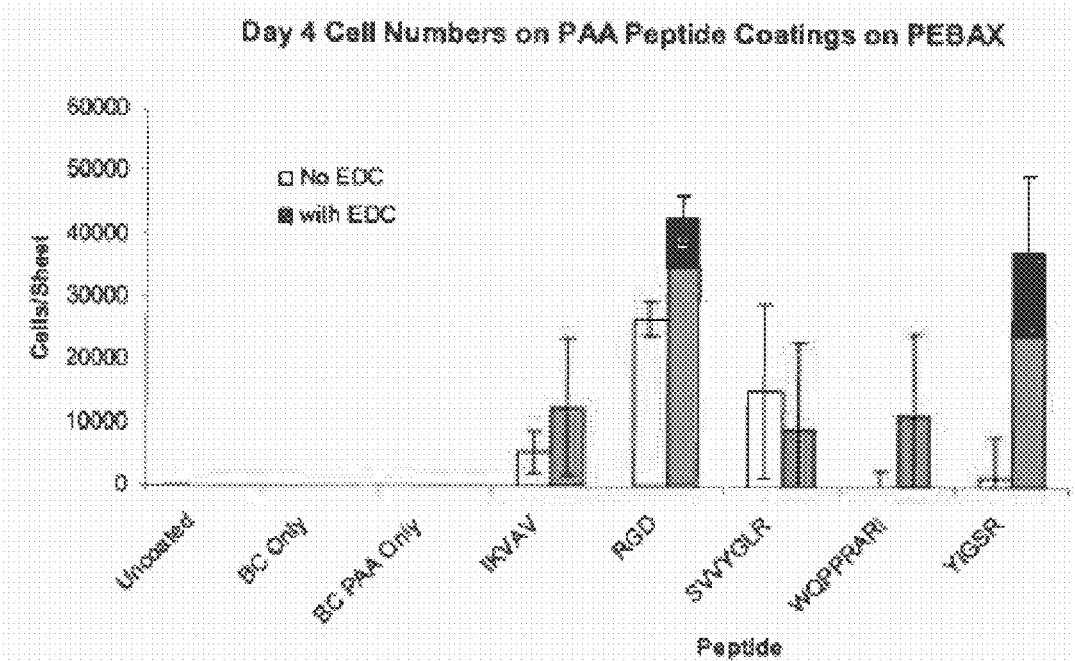

Human Coronary Artery Endothelial Cells (HCAECs) and Endothelial Growth Medium Two Microvascular (EGM-2MV) were from Lonza (Walkersville MD). HCAECs were grown to confluency in tissue culture polystyrene flasks and collected by trypsinization followed by neutralization of trypsin with EGM-2MV. Cells were counted using a hemacytometer prior to seeding on coated PEBAX. PEBAX strips (1×1 cm) were placed in a 24 well cell culture plate and then 1 ml of EGM-2MV containing 100,000 HCAECs was added to the plate and incubated for 2 hours. A standard curve of HCAECs ranging from 100,000 to 1.563 cells per well in 24 well cell culture plates was also prepared by serial dilution. After the 2 hour incubation. PEBAX strips were rinsed 3 times in Dulbecco's Phosphate Buffered Saline (DPBS, Lonza) and then transferred to a new 24 well plate containing 1 ml of fresh EGM-2MV. 0.2 mL of CellTiter-Bluet (Promega, Madison. WI) was then added to the plates containing PEBAX and the cell standards and incubated for 1.5 hours and then collected and read on a fluorescent plate reader with excitation of 560 nm and emission at 590 nm. PEBAX was then rinsed in DPBS and placed into new culture plates containing EGM-2MV for an additional 4 days at which point the number of attached cells was quantified again using CellTiter-Blue®. Results of initial attachment and the day 4 quantification are shown in FIGS. 13A and 13B. HCAECs showed no attachment on uncoated PEBAX or PEBAX receiving only coating solution A (BC Only) or coating solution A and D only (BC PAA Only). All peptide coatings increased cell attachment and attachment was higher when EDC/NHS was included in the peptide coating solution (with EDC).

Example 7: Hemocompatibility Assay

Coatings having a poly(acrylic acid) (PAA) top coating and comparative coatings were tested for hemocompatibility properties. Braided nitinol embolic protection devices were cleaned in IPA followed by a solution of hot 10% Valtron SP220M (Valtech. Corp., Pottstown, PA). A tielayer of methylhydrosiloxane-dimethylsiloxane copolymer (Gelest, Morrisville, PA) was deposited on the device by dipping followed by a 35 minute bake at 120° C., and rinsing in IPA. A basecoat of photo-PVP and BBP at 10 and 0.2 mg/ml respectively was prepared in 75% IPA/25% water and applied by spray coating using an EFD sprayer (Nordson EFD, Westlake, OH). After spray coating parts were exposed to UV for 1 minute. Parts were then dipped in PAA coating solution D, dried and exposed to UV for 1 minute.

Figure 14:
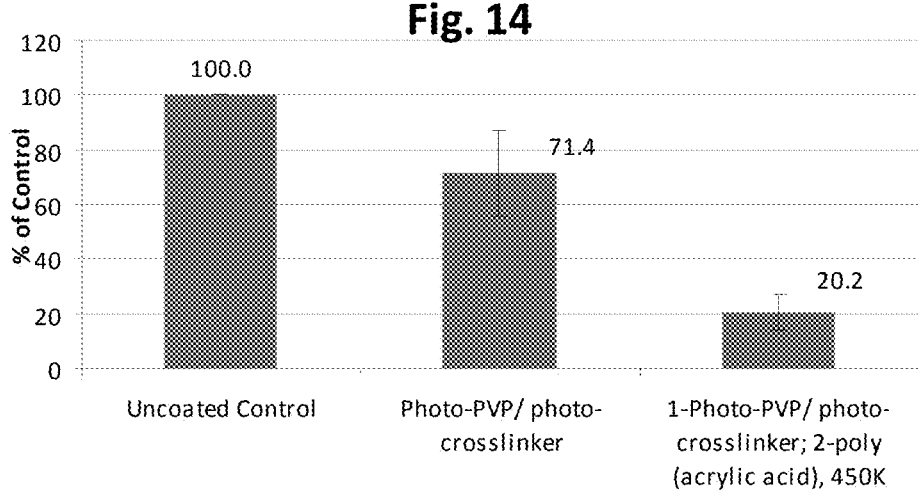
FIG. 14 is a graph showing results of a hemocompatibility assay measuring platelet presence (amount) on various coated substrates as compared to an uncoated control.

Coated and uncoated devices were tested in an in vitro bifurcated bovine blood loop. Platelets were radiolabeled with indium-111 to allow for thrombus quantification. The flow rate of blood was set to 40 mL/min and experiments were terminated when the flow of any one device dropped by 50%, which generally took 20 to 40 minutes. At the end of the experiment, each device was placed in a gamma counter to measure for adherent thrombus. Filters coated with a poly(acrylic acid) top coat on a base coat formed from photo-PVP and photo cross-linker reduced thrombus formation better than devices coated only with the photo-PVP and photo cross-linker (FIG. 14).

Figure 15:
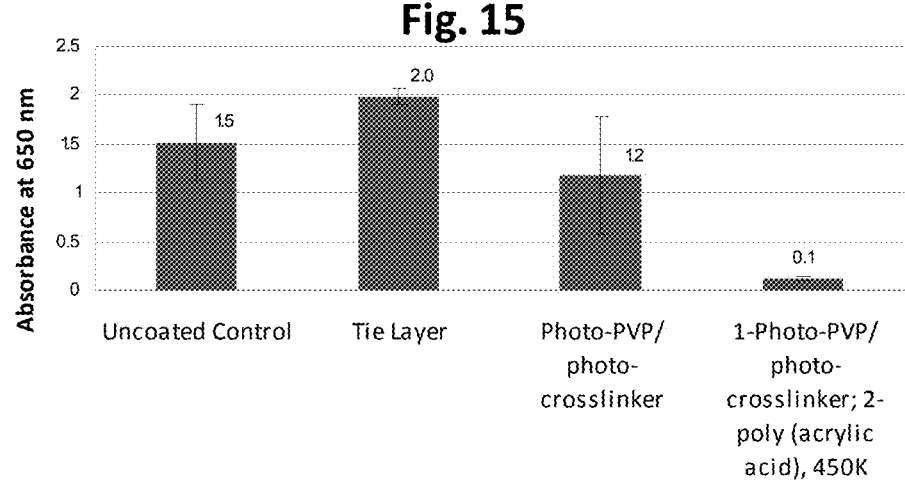
FIG. 15 is a graph showing results of an in vitro fibrinogen immunoassay measuring absorption from human platelet poor plasma to various coated substrates.

Coated and uncoated devices were also tested for fibrinogen adsorption using an immunoassay. Devices were incubated in human platelet poor plasma for 2 hours and then rinsed in phosphate buffered saline with tween. Devices were then exposed to a horseradish peroxidase (HRP) labeled anti-human fibrinogen antibody (Rockland Immunochemicals, Gilbertsville, PA) and rinsed again. Devices were then placed in a tetramethylbenzidine (TMB) substrate (SurModics BioFx, Eden Prairie, MN) for 15 minutes and the absorbance was measured at 650 nm using a spectrophotometer. Fibrinogen adsorption was significantly less on the coating with the poly (acrylic acid) top coat compared to the photo-PVP and photo-crosslinker base coat alone (FIG. 15).

It should be noted that, as used in this specification and the appended claims, the singular forms "a," "an." and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which the disclosure pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The disclosure has been described with reference to various specific and preferred embodiments and techniques. However, it should be understood that many variations and modifications may be made while remaining within the spirit and scope of the disclosure.

What is claimed is:

1. A lubricious coating comprising:
a first coated layer comprising a vinyl pyrrolidone polymer and photoreactive groups, wherein the photoreactive groups are pendent from the vinyl pyrrolidone polymer or on a first cross-linking agent comprising at least two photoreactive groups, or both; and
a second coated layer that is different in composition than the first coated layer and is a top coating comprising an acid polymer, wherein the second coated layer is in direct contact with the first coated layer, wherein the first coated layer is between the second coated layer and a substrate surface,
wherein (a) the acid polymer is formed from a composition comprising one or more of the following monomers: acrylic acid, methacrylic acid, itaconic acid, monomethyl itaconic acid, maleic anhydride, fumaric acid, crotonic acid, acrylamido-2-methylpropanesulfonic acid (AMPS), 2-(meth)acrylamido-2-methylpropane sulfonic acid, vinyl sulfonic acid, 2-sulfoethyl methacrylate, and salts thereof, or (b) the acid polymer is a sulfonic acid polymer, a carboxylic acid polymer, or a phosphonic acid polymer.

2. The coating of claim 1 wherein the second coated layer further comprises an acrylamide polymer comprising at least one photo reactive group, optionally wherein the acrylamide polymer comprises acrylamide-, sulfonate-, and alkylene oxide-containing subunits.

3. The coating of claim 2, wherein the vinyl pyrrolidone polymer and the acrylamide polymer are present in the coating at a weight ratio in the range of approximately 3:1 to 1:3 (wt./wt.), respectively.

4. The coating of claim 2, wherein the acid polymer and the acrylamide polymer are present in the coating at a weight ratio in the range of approximately 2:1 to 1:2 (wt./wt.), respectively.

5. The coating of claim 1 comprising a first or second cross-linking reagent, wherein at least one of the first and second cross-linking agent(s) is a compound of formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom, optionally wherein at least one of the first and second cross-linking agents is a compound of formula selected from:

(a)

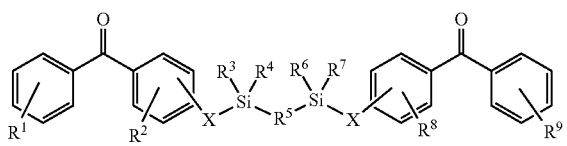

wherein $R^1$, $R^2$, $R^8$ and $R^9$ are any substitution; $R^3$, $R^4$, $R^6$ and $R^7$ are alkyl, aryl, or a combination thereof; $R^5$ is any substitution; and each X, independently, is O, N, Se, S, or alkyl, or a combination thereof;

(b)

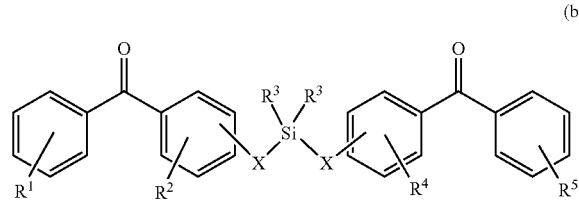

wherein $R^1$ and $R^5$ are any substitution; $R^2$ and $R^4$ can be any substitution, except OH; $R^3$ can be alkyl, aryl, or a combination thereof; and each X, independently, is O, N, Se, S, alkyl or a combination thereof;

(c)

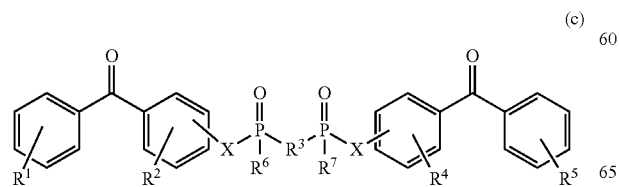

wherein $R^1$, $R^2$, $R^4$ and $R^5$ are any substitution; $R^3$ is any substitution; $R^6$ and $R^7$ are alkyl, aryl, or a combination thereof, and each X, independently, is O, N, Se, S, alkyl, or a combination thereof; and (d)

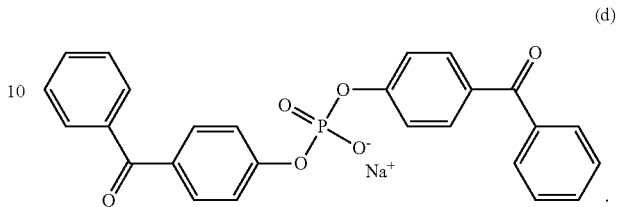

6. The coating of claim 1, wherein the acid polymer is an acrylic acid polymer that has an average molecular weight of 150 kDa or greater.

7. The coating of claim 1, wherein:
(I) the coating releasing particulates of less than 3,000 particles greater than 10 microns; or
(II) (a) the coating exhibits a lubricity when wetted of between 0 and 30 grams of force for at least 10 consecutive testing cycles, or wherein (b) the coating exhibits a durability of lubricity such there is less than a 30 percent increase in measured friction between the average of cycles 1-5 of testing and cycles 10-15 of testing, or both (a) and (b).

8. The coating of claim 1, wherein the thickness of the first and second coated layers combined is in the range of about 100 to 1000 nm when dry.

9. The coating of claim 1, wherein the first coated layer does not include the acid polymer of the second coated layer, and the second coated layer does not include the vinyl pyrrolidone polymer of the first coated layer.

10. A medical device comprising the coating of claim 1.

11. The medical device of claim 10, wherein the substrate comprises polyamide, polyimide, polyether block amide (PEBAX), polyether ether ketone (PEEK), high density polyethylene (HDPE), polyethylene, polyurethane, or polyethylene vinyl acetate.

12. The medical device of claim 10, the medical device comprising a catheter.

13. The medical device of claim 10, wherein the catheter is selected from the group consisting of venous access catheters, vascular access catheters, angioplasty catheters, cardiac catheters, balloon catheters, drug infusion catheters, intravenous catheters, stroke therapy catheters, and stent graft catheters.

14. A method making a coating according to claim 1 on a medical device comprising:
applying a first coating solution directly or indirectly on a medical device surface, the first coating solution comprising a vinyl pyrrolidone polymer and photoreactive groups, wherein the photoreactive groups are pendent from the vinyl pyrrolidone polymer or present on a first cross-linking agent comprising at least two photoreactive groups; and a first solvent, and drying the first coating solution;
exposing the first coating solution to actinic radiation to form a first layer;
applying a second coating solution onto the first layer, wherein the second coating solution is different in composition than the first coating solution, the second coating solution comprising an acid polymer wherein (a) the acid polymer is formed from a composition comprising one or more of the following monomers: acrylic acid, methacrylic acid, itaconic acid, monomethyl itaconic acid, maleic anhydride, fumaric acid, crotonic acid, acrylamido-2-methylpropanesulfonic acid (AMPS), 2-(meth)acrylamido-2-methylpropane sulfonic acid, vinyl sulfonic acid, 2-sulfoethyl methacrylate, and salts thereof, or (b) the acid polymer is a sulfonic acid polymer, a carboxylic acid polymer, or a phosphonic acid polymer, and a second solvent, and optionally a second cross-linking agent comprising at least two photoreactive groups, and drying the second coating solution; and exposing the second coating solution to actinic radiation to form a second layer.

15. The coating of claim 1 wherein the acid polymer is a copolymer made from two or more different acid-group containing monomers, or is a copolymer made from one or more acid-group containing monomer(s) and one or more non-acid group containing monomer(s), wherein optionally the copolymer is a random copolymer, a block copolymers, a graft copolymer, or a blends thereof.

16. The lubricious coating of claim 1 where, in the first coated layer the vinyl pyrrolidone polymer is the sole polymeric component, and in the second coated layer the acid polymer is the sole polymeric component.

17. The lubricious coating of claim 1 wherein the first coated layer consists essentially of the vinyl pyrrolidone polymer and the photoreactive groups, and the second coated layer consists essentially of the acid polymer.

* * * * *